United States Patent
Mitchell et al.

(10) Patent No.: US 9,504,371 B2
(45) Date of Patent: *Nov. 29, 2016

(54) ENDOSCOPIC SYSTEM WITH TORQUE TRANSMITTING SHEATH

(71) Applicant: USGI Medical, Inc., San Clemente, CA (US)

(72) Inventors: Sean Mitchell, Oceanside, CA (US); Richard C. Ewers, Fullerton, CA (US); Tracy D. Maahs, Yorba Linda, CA (US)

(73) Assignee: USGI Medical, Inc., San Clemente, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/612,118

(22) Filed: Feb. 2, 2015

(65) Prior Publication Data

US 2015/0173589 A1  Jun. 25, 2015

Related U.S. Application Data

(63) Continuation of application No. 14/141,237, filed on Dec. 26, 2013, now abandoned, which is a continuation of application No. 13/483,371, filed on May 30, 2012, now abandoned, which is a continuation-in-part of application No. 12/061,591, filed on Apr. 2, 2008, now Pat. No. 9,055,864.

(51) Int. Cl.
| | |
|---|---|
| *A61B 1/00* | (2006.01) |
| *A61M 25/00* | (2006.01) |
| *A61B 1/005* | (2006.01) |
| *A61M 25/01* | (2006.01) |
| *A61B 1/008* | (2006.01) |
| *A61B 1/012* | (2006.01) |

(52) U.S. Cl.
CPC .............. *A61B 1/0057* (2013.01); *A61B 1/008* (2013.01); *A61B 1/0052* (2013.01); *A61B 1/0055* (2013.01); *A61B 1/012* (2013.01); *A61M 25/0147* (2013.01)

(58) Field of Classification Search
USPC ........ 600/104, 106, 107, 114, 115, 139–152; 604/95.01–95.05, 523–528; 606/1
See application file for complete search history.

(56) References Cited

U.S. PATENT DOCUMENTS

| | | |
|---|---|---|
| 3,557,780 A | 1/1971 | Sato |
| 4,873,965 A | 10/1989 | Danieli |

(Continued)

OTHER PUBLICATIONS

United States Patent and Trademark Office, International Search Report and Written Opinion for PCT/US13/39672 (Jul. 29, 2013).

*Primary Examiner* — Ryan Henderson
(74) *Attorney, Agent, or Firm* — Kenneth H. Ohriner; Perkins Coie LLP

(57) ABSTRACT

An endoluminal surgical instrument has first and second steering controls on a handle. A flexible shaft attached to the handle has a distal steerable end including a first link and a second link separated by a plurality of intermediate links. First and second steering elements, such as pairs of steering wires, are linked to first and second steering controls and to the first and second links. One or more of the links is pivotable through an angle of at least 30 degrees relative to an adjoining link. The set back position of the second steering elements from the first steering elements, and the pivoting capability of the links allows the steerable end to be steered into a small bend radius. This makes the instrument highly maneuverable for use in endoluminal surgery, such as incision-less surgery of the stomach.

8 Claims, 27 Drawing Sheets

(56) References Cited

U.S. PATENT DOCUMENTS

| | | |
|---|---|---|
| 5,329,887 A | 7/1994 | Ailinger et al. |
| 5,448,989 A | 9/1995 | Heckele |
| 5,575,755 A | 11/1996 | Krauter et al. |
| 6,960,163 B2 | 11/2005 | Ewers et al. |
| 7,637,905 B2 | 12/2009 | Saadat et al. |
| 7,837,615 B2 | 11/2010 | Le et al. |
| 2004/0044270 A1 | 3/2004 | Barry |
| 2004/0249367 A1 | 12/2004 | Saadat et al. |
| 2005/0272977 A1 | 12/2005 | Saadat et al. |
| 2006/0058582 A1 | 3/2006 | Maahs et al. |
| 2006/0111615 A1 | 5/2006 | Danitz et al. |
| 2006/0178562 A1 | 8/2006 | Saadat et al. |
| 2007/0049800 A1 | 3/2007 | Boulais |
| 2007/0255102 A1* | 11/2007 | Maruyama ............ 600/146 |
| 2007/0255103 A1 | 11/2007 | Maruyama |
| 2008/0262294 A1 | 10/2008 | Ewers et al. |
| 2008/0262300 A1 | 10/2008 | Ewers et al. |
| 2009/0253961 A1 | 10/2009 | Le et al. |
| 2010/0286478 A1 | 11/2010 | Ewers et al. |

\* cited by examiner

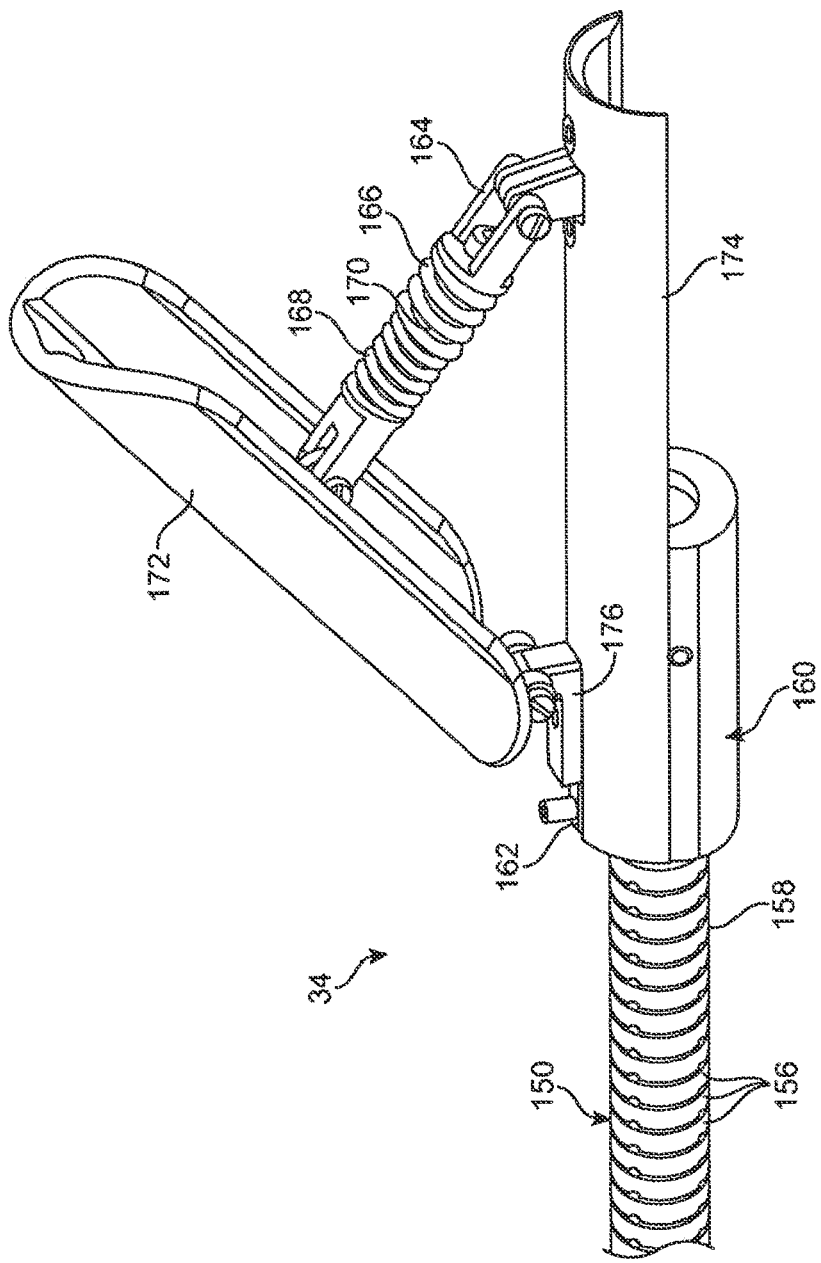

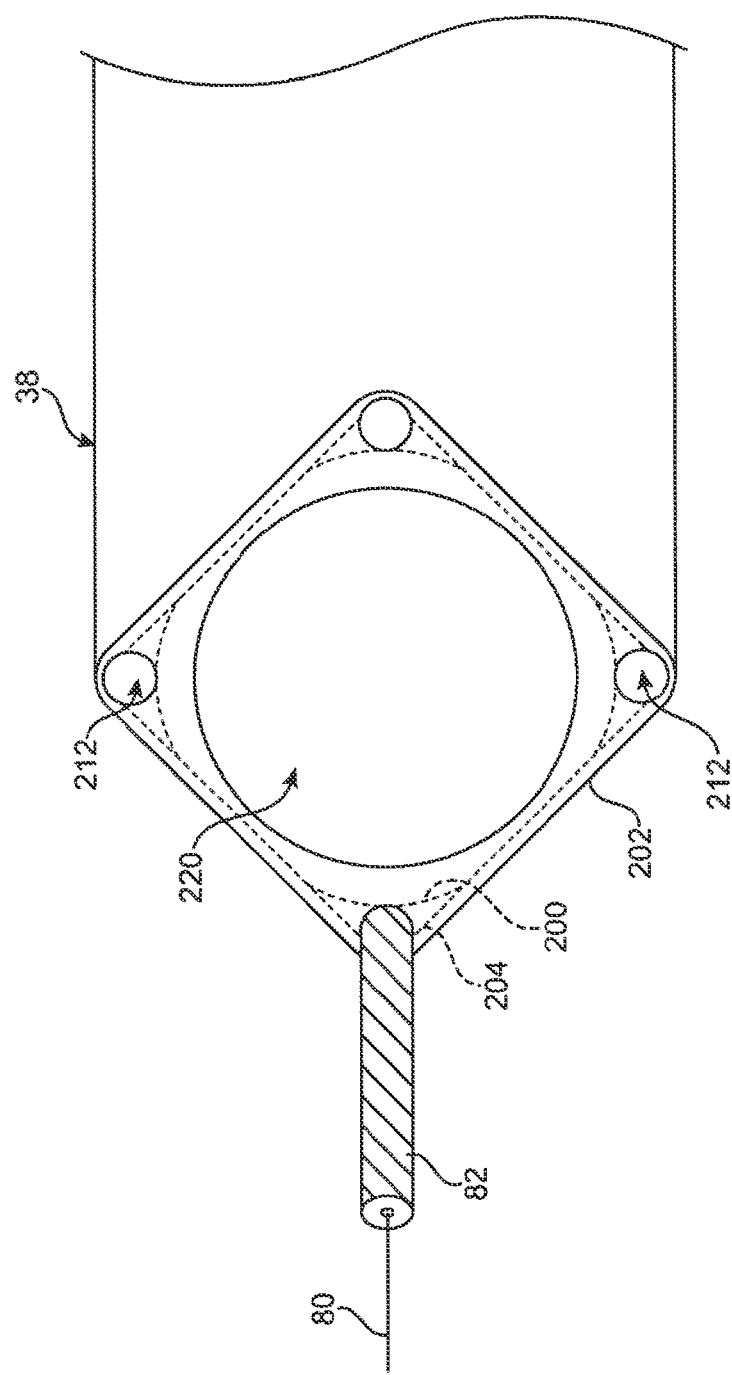

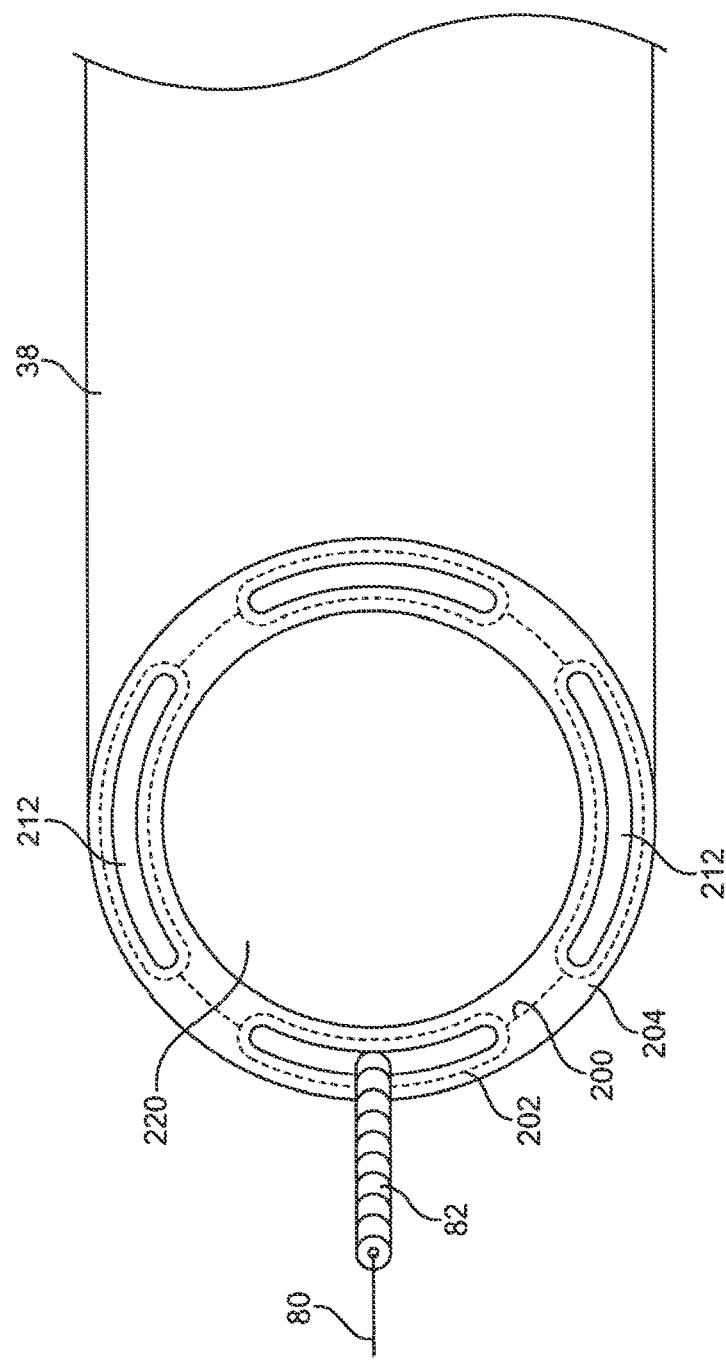

ENDOSCOPIC SYSTEM WITH TORQUE TRANSMITTING SHEATH

CROSS-REFERENCES TO RELATED APPLICATIONS

This Application is a Continuation of U.S. patent application Ser. No. 14/141,237 filed Dec. 26, 2013 and now pending, which is a Continuation of U.S. patent application Ser. No. 13/483,371 filed May 30, 2012 and now abandoned, which is a Continuation-in-Part of U.S. patent application Ser. No. 12/061,591 filed Apr. 2, 2008, and now pending. Each of these applications is incorporated herein by reference.

BACKGROUND

Endoscopy is a minimally invasive medical procedure used to view areas inside of the body. By inserting an endoscope into the body, generally (but not necessarily) through a natural body opening, interior areas of the body may be viewed. Since endoscopic diagnoses or surgery do not require the types of large incisions that occur during conventional surgery, risks of complications are reduced and recovery tends to be relatively quick and painless in relation to conventional surgery.

The endoscope typically has a long thin flexible tubular body containing wiring and/or fiber optics to illuminate the viewing site and to transmit images of the viewing site to an eyepiece at the back end of the endoscope. The image may also be displayed on a video screen. The endoscope may also provide insufflation, irrigation, and/or suction. Endoscopic systems or tools are typically used with endoscopes to perform cutting, piercing, stitching, holding, etc. during endo-surgery.

Various endoscopic systems have been successfully used to perform a wide variety of diagnostic and surgical procedures. These include shapelocking tools, guides, or assemblies that provide advantages over conventional endoscopy or endosurgery. However, typical shapelocking assemblies include multiple highly engineered and precision manufactured components. As a result, they tend to be relatively more expensive and are intended to be reused many times. On the other hand, many components of endoscopic systems are well suited for single use only, because they are low cost or wear out too quickly to allow for safe and reliable reuse.

In addition various endoscopic procedures are more effectively performed using endoscopic systems having varying features and capabilities. For example, some endoscopic procedures are more effectively performed using an endoscopic system having a shapelocking assembly, while other endoscopic procedures are more effectively performed using an endoscopic system having an elongated shaft that is flexible but not necessarily rigidizable. Other system capabilities, such as steerability, may be preferred for certain other procedures.

Accordingly, engineering challenges remain in designing endoscopic or endosurgical systems that achieve the advantages of using both reusable and disposable assemblies or components. In particular, these challenges remain in designing systems having modular components having various desirable functional capabilities that are capable of being exchanged, switched out, or otherwise selected by the user for use during a particular procedure.

SUMMARY

In a first aspect, an endoscopic system has an elongated, tubular, flexible body member that is adapted to be used to perform diagnostic or therapeutic endoscopic procedures. The endoscopic system includes a first sub-assembly and a second sub-assembly that are combined to form the elongated, tubular, flexible body. In an embodiment, the first sub-assembly comprises a body member that provides structural support for the endoscopic system and the second sub-assembly comprises a sheath member that substantially maintains the first sub-assembly in a relatively clean or sterile condition. The endoscopic system also includes one or more control mechanisms configured to provide an interface for the user to operate the endoscopic system. In an embodiment, the one or more control mechanisms are provided on the first sub-assembly. In other embodiments, the one or more control mechanisms are provided on the second sub-assembly, or on both the first and second sub-assemblies.

In several embodiments, the endoscopic system includes a single use assembly and a reusable assembly. The single use assembly includes components adapted to act as a barrier against body fluids, to maintain the reusable assembly in a relatively clean or sterile condition. The single use assembly components are also adapted to support, position, hold, guide or steer endoscopic and endosurgical devices. The reusable assembly is configured to provide a shapelocking capability. The combination of the single use assembly and the reusable assembly provides versatile yet cost effective endoscopic systems.

In a second aspect, an endoscopic system has a handle and an elongated, tubular, flexible shaft that is adapted to be used to perform diagnostic or therapeutic endoscopic procedures. The endoscopic system shaft includes an outer layer, a body member, and an inner layer. Each of the outer and inner layers comprises a braided or woven reinforcement material adapted to provide improved torque transmission. In some embodiments, the body member comprises a coil.

In a third aspect, a steering mechanism includes a first knob attached to a first pulley, and a second knob attached to a second pulley. Each of the pulleys is attached to one or more steering wires. An indexing and locking mechanism is adapted to selectively engage and lock a selected one (or both) of the pulleys to provide indexed steering and locking.

In a fourth aspect, a tool locking mechanism includes a plunger that is housed within an access port and that is selectively advanced into and withdrawn from a tool lumen by rotation of a lever having a cam surface.

In a fifth aspect, an endoluminal surgical instrument has first and second steering controls on a handle. A flexible shaft attached to the handle has a distal steerable end including a first link and a second link separated by a plurality of intermediate links. First and second steering elements, such as pairs of steering wires, are linked to first and second steering controls and to the first and second links. One or more of the links is pivotable through an angle of at least 30 degrees relative to an adjoining link. The set back position of the second steering elements and the pivoting capability of the links allows the steerable end to be steered into a small bend radius. This makes the instrument highly maneuverable for use in endoluminal surgery, such as incision-less surgery of the stomach.

BRIEF DESCRIPTION OF THE DRAWINGS

In the drawings.

FIG. 8B is an enlarged front, top, and left side perspective view of the back end of the shapelock assembly shown in FIG. 7B.

FIG. 11A is a schematically illustrated section view taken along line 11-11 of FIG. 9.

FIG. 11B is a schematically illustrated section view of an alternative embodiment of the system of FIG. 9.

DETAILED DESCRIPTION OF THE DRAWINGS

As used herein, the term "endoscopic" means of, relating to, or performed by means of and endoscope or endoscopy, and includes viewing, manipulating, treating, or performing surgery on or at a site inside of the body, without opening up the body or only minimally opening up the body. Hence, as used herein, endoscopic includes endosurgical, endoluminal, laparoscopic, and the like. As used herein, the term "shapelock assembly" means an apparatus that may be transitional or switched (in whole or in part) between a generally flexible condition and a generally rigid condition. Several examples of shapelock assemblies are described, for example, in U.S. Pat. Nos. 6,783,491 and 6,960,163: and United States Patent Application Publication No. US 2006/005852, each of which is incorporated by reference herein.

Figure 1:
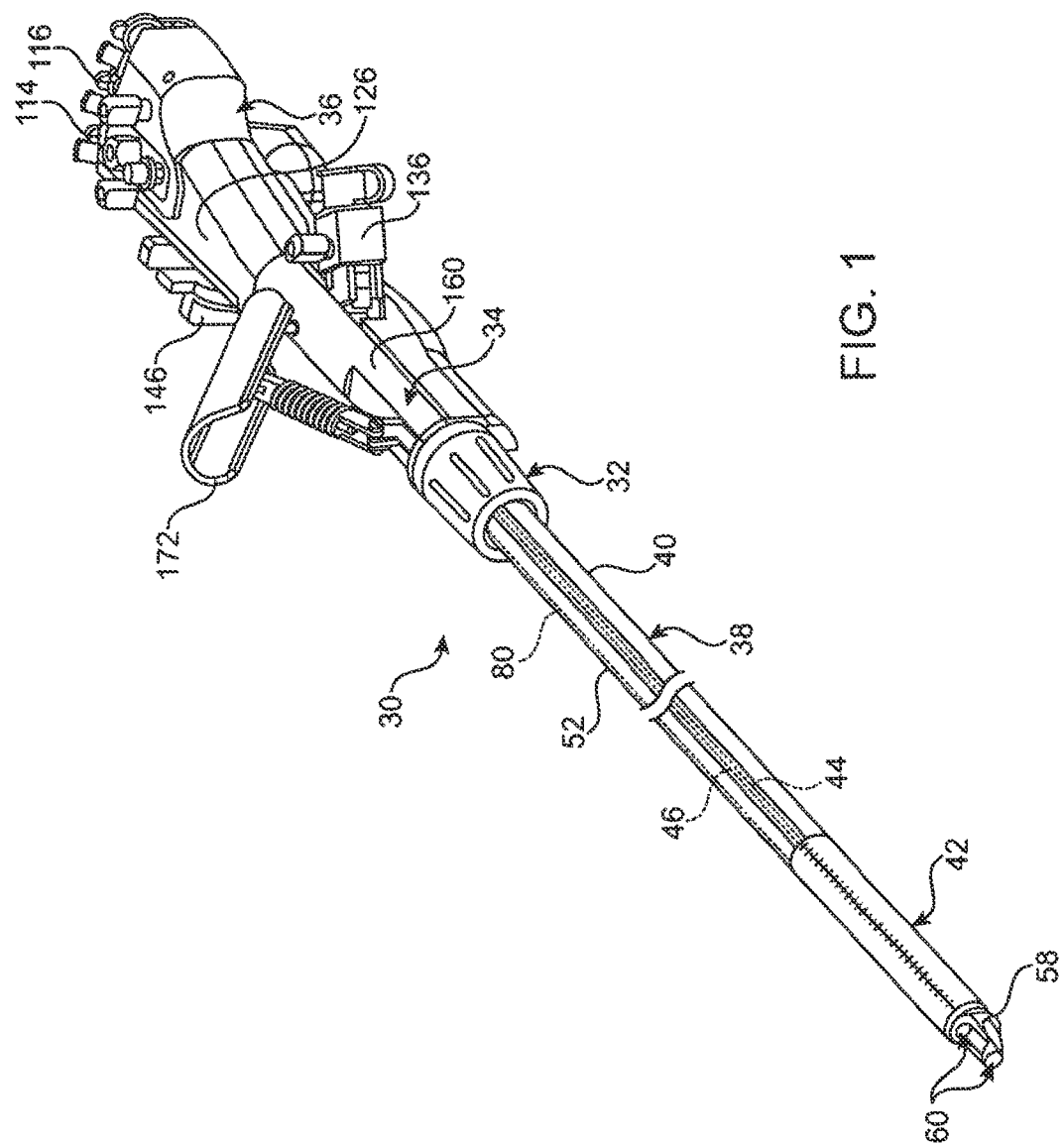
FIG. 1 is a front, top, and left side perspective view of an endoscopic system.
Figure 2:
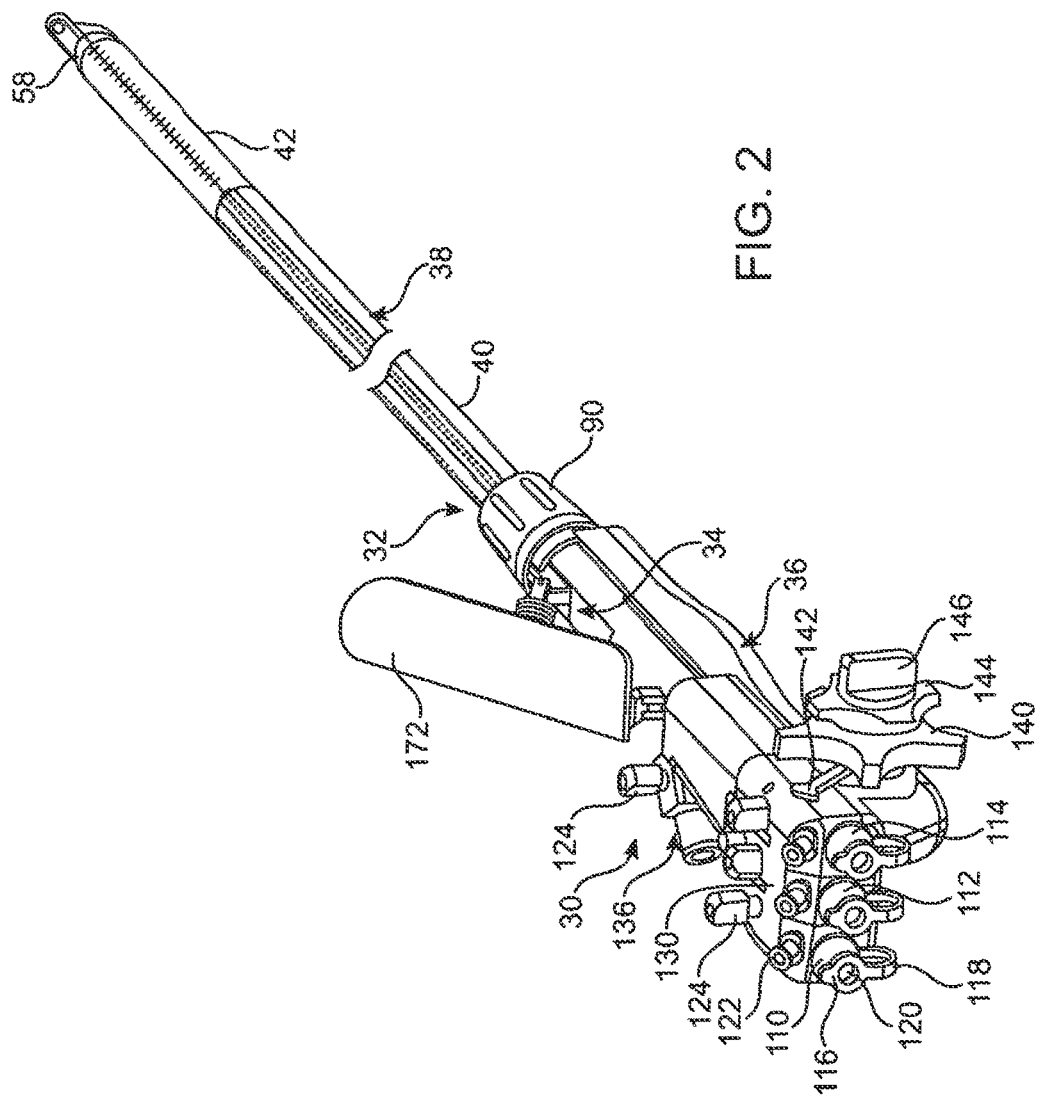
FIG. 2 is a top, back, and right side perspective view of the system shown in FIG. 1.

Turning to the drawings, as shown in FIGS. 1 and 2, an embodiment of an endoscopic system 30 includes a reusable shapelock assembly 34 that is adapted for use within a disposable assembly generally designated 32. The disposable assembly 32 has a flexible sheath 38 attached to a relatively rigid handle 36.

Figure 3:
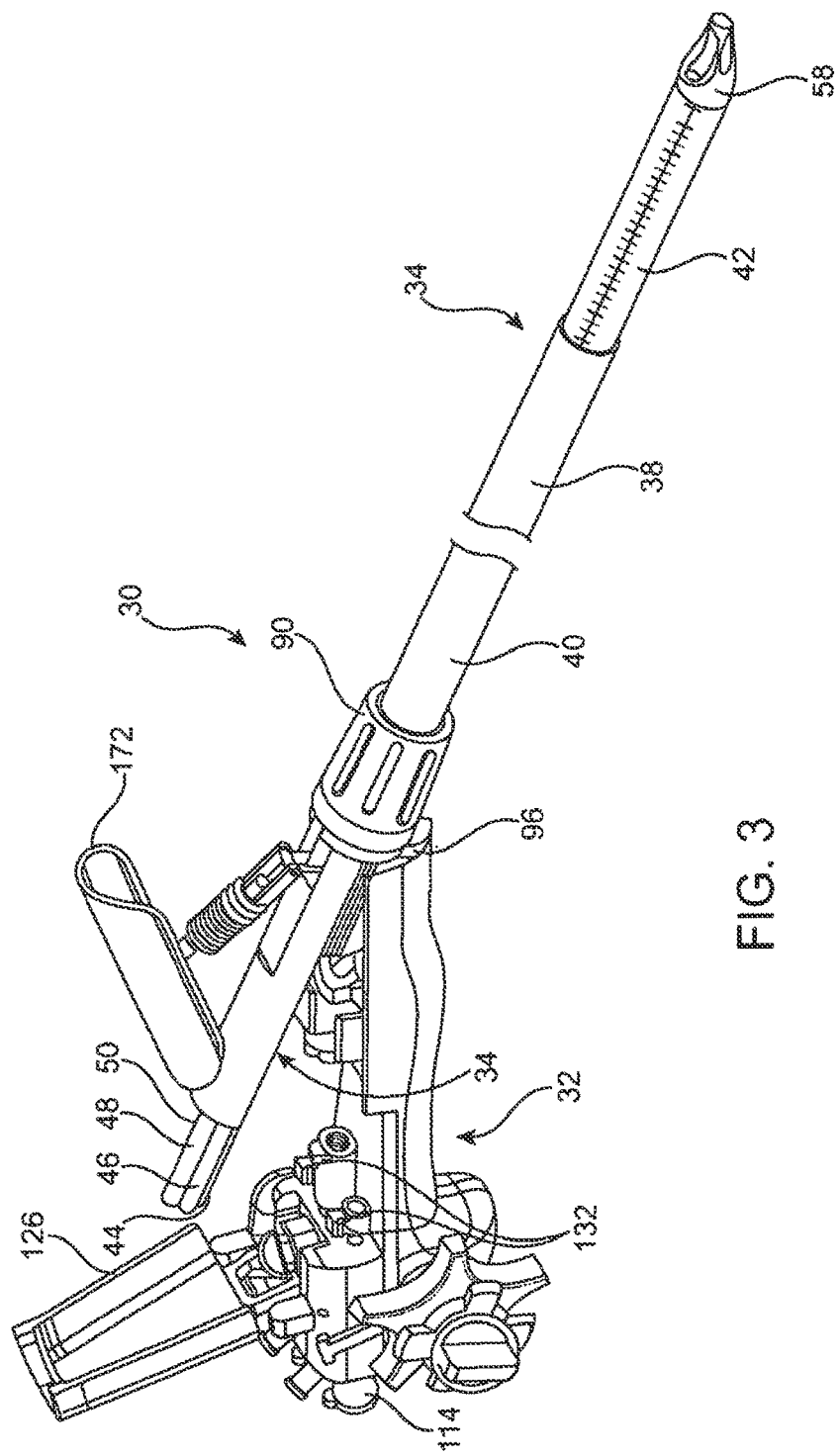
FIG. 3 is a front, top, and right side perspective view of the system shown in FIG. 1, during an intermediate assembly step.
Figure 4:
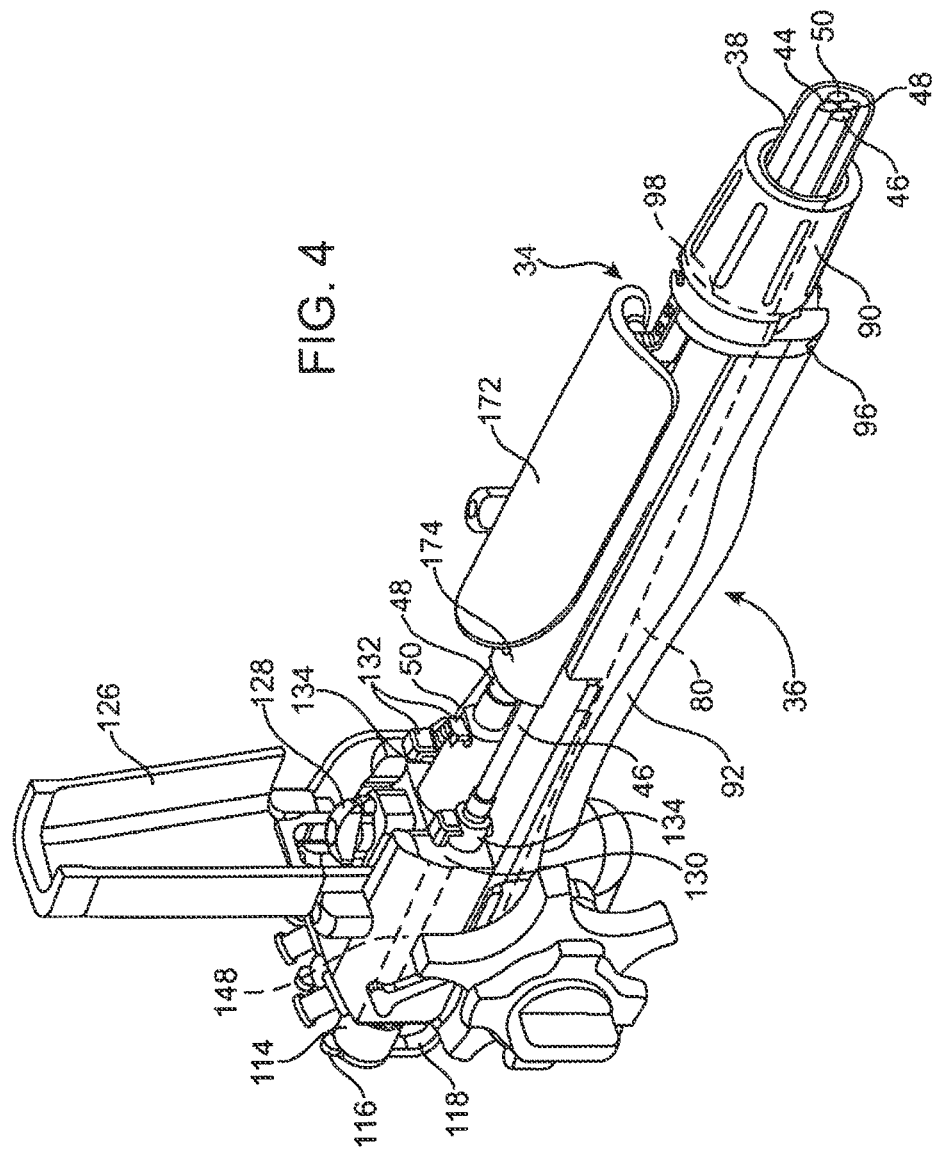
FIG. 4 is an enlarged front, top, and right side perspective view of the handle portion of the system shown in FIG. 1.
Figure 5:
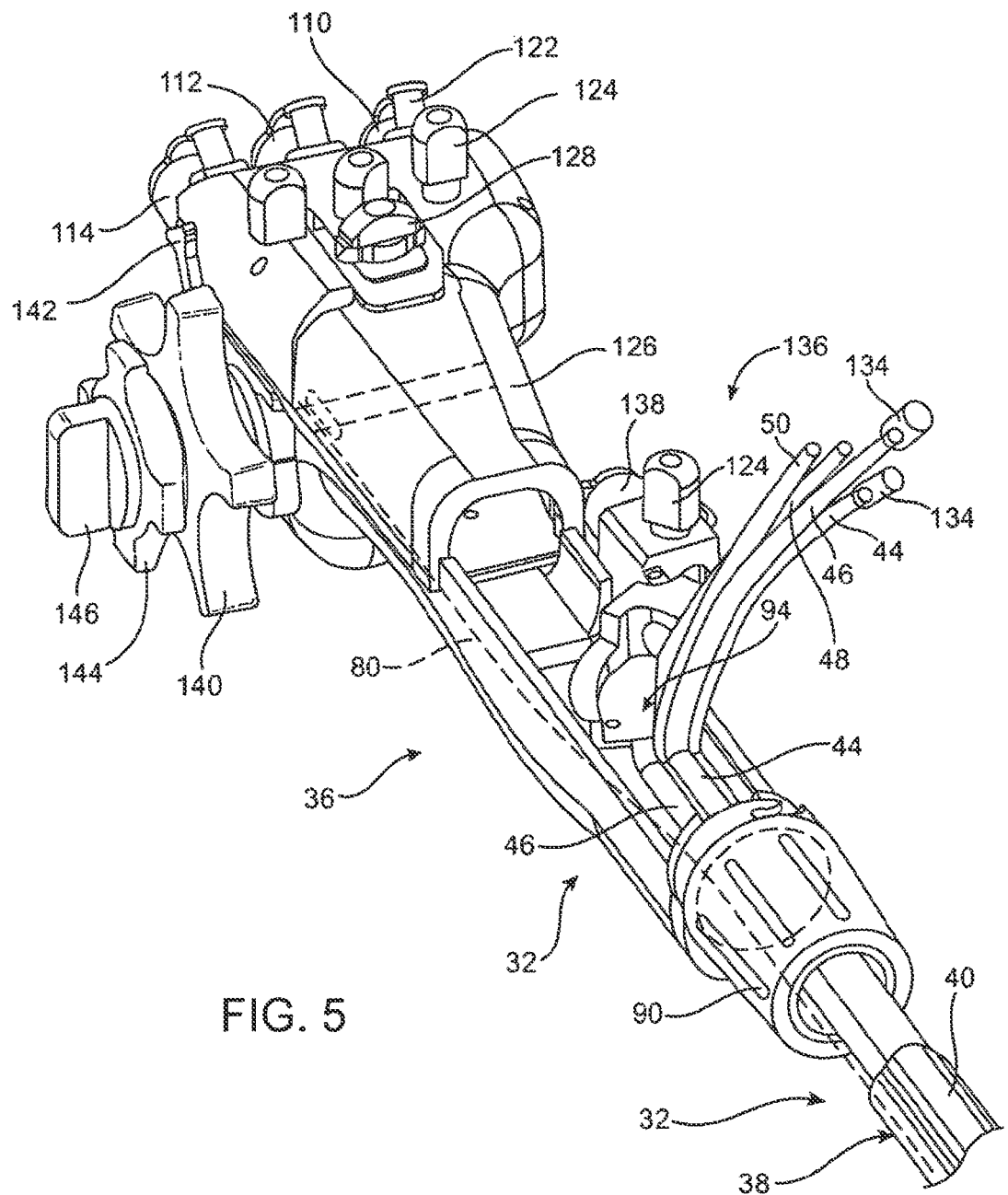
FIG. 5 is an enlarged front, top, and right side perspective view of the system shown in FIG. 1, before complete assembly.

Referring also to FIGS. 3, 4, and 5, the sheath 38 includes a tip 58 attached to the distal end of a steerable section 42. A body section 40 of the sheath 38 extends proximally from the steerable section 42 to the handle 36. A lock nut 90 or similar attachment holds the proximal end of the body section 40 of the sheath 38 onto the handle 36.

Figure 9:
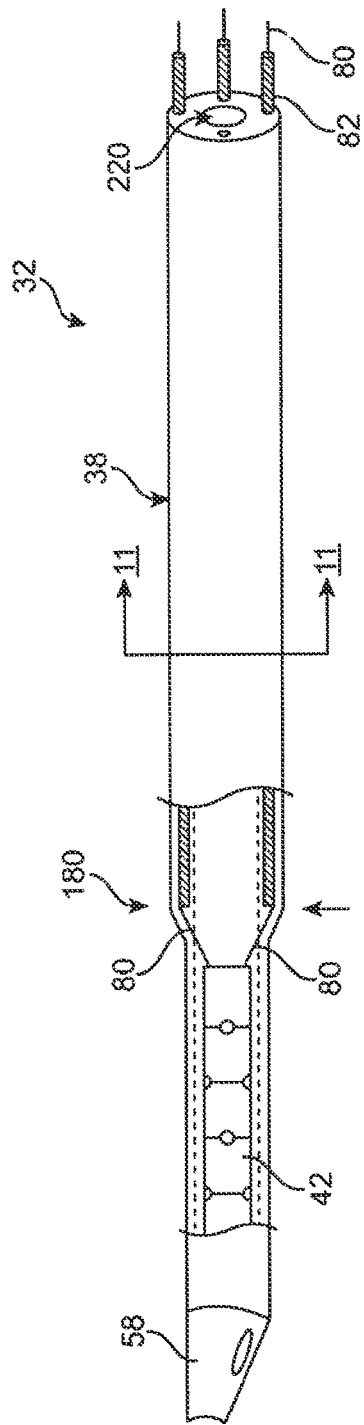
FIG. 9 is a schematically illustrated side view of a sheath portion of the endoscopic system shown in FIG. 1.
Figure 10:
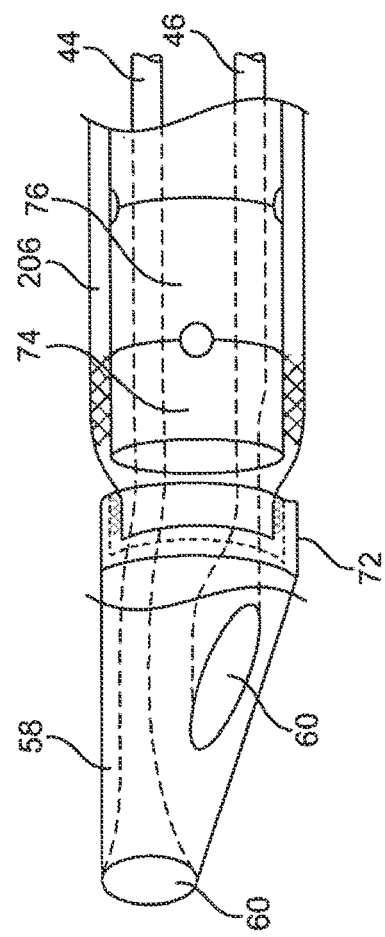
FIG. 10 is an enlarged schematically illustrated side view of the sheath tip shown in FIG. 9.

Referring to FIGS. 9 and 10, the sheath tip 58 has one or more tool lumen openings 60. A plurality of tool lumens extend through the interior of the sheath 38. The tool lumens are defined by one or more structural guide way members provided within the interior of the sheath 38. In the embodiments shown, the tool lumens are defined by a plurality of sleeves or tubes 44, 46, 48, and 50, each of which has an open distal end that is sealed around a respective lumen opening 60 in the tip 58. The tubes 44, 46, 48, and 50 extend proximally from the tip 58 through the length of the sheath 38 to the handle 36. In an embodiment, the tubes 44-50 are flexible rubber or plastic tubes that act as guide ways between the handle 36 and the tip 58 for tools and instruments, as described below. In other embodiments, the tubes 44-50 are flexible tubes having composite construction, such as a multi-layer extrusion, or coil and/or braid reinforced construction. In some embodiments, the tubes 44-50 are constructed to reduce or eliminate the likelihood that the tubes will become twisted, kinked, tangled, torn, or that the lumens defined by the tubes would collapse under vacuum.

The embodiments described above and illustrated in the Figures include a plurality of tubes that serve as structural guide way members used to define the tool lumens extending through the sheath 38. In other embodiments, the tool lumens are defined by other structures that serve as guide way members. For example, in some embodiments, the tool lumens are defined by one or more partition members extending partially or completely through the sheath 38. In an embodiment, the partition members define tool lumens having a circular cross-section, while in other embodiments the partition members define lumens having non-circular (e.g., triangular, rectangular, square, oval, irregular, or other) cross-sectional shapes. In an embodiment, the partition members are removably attached to the interior of the sheath. In other embodiments, the partition members are formed integrally (e.g., co-extruded) with the sheath.

Referring still to FIGS. 9 and 10, an embodiment of the steerable section 42 at the distal end of the sheath 38 is formed by segments, links, or other generally rigid and pivotably interconnected elements. In the example shown in FIGS. 9 and 10, the steerable section 42 includes links, with the first link shown at 74 and the second link at 76. The length and flexibility of the steerable section 42 is varied by selecting the number and size of the individual links making up the steerable section 42. Steering wires 80 or other steering elements are typically attached to the first link 74, for steering the steerable section 42. The steering wires 80 extend proximally from the first link 74, through the second link 76 and any additional links of the steering section 42, and through the sheath 38 to the handle 36. In an embodiment, the steering wires 80 are provided within coils 82 or other column strength element. The coils 82 allow the steering wires 80 to be tensioned without buckling the sheath 38. The steering section generally is about 4-10 cm long, whereas the sheath 38 is typically between 20-200 cm. The sheath outer diameter is typically 1-2.5 cm.

While FIGS. 9 and 10 show the steerable section 42 operated via steering wires 80, other forms of steering elements may be used, including elements acting in tension, such as steering wires, or elements acting in compression, such as push rods. The steering section 42 may alternatively be controlled electrically, pneumatically, or hydraulically. The specific technique used for controlling the steerable section 42 may vary.

Referring to FIG. 10, the sheath 38 has an outer skin or layer 206 formed of a material that is flexible and that provides a protective layer to prevent passage of bodily fluids, gases, and other materials, such as a polymeric or plastic material or the like. In an embodiment, the cylindrical proximal end 72 of the tip 58 is sealed onto the outer skin 206 via an adhesive or other bonding or attachment method. In other embodiments, the tip 58 is removably attached to the distal end of the sheath 38, such as by screwing, friction fit, or other mechanism adapted to provide the user with the ability to exchange tips for various procedures. In an embodiment, the tip 58 is made of hard or soft plastic or rubber, or similar non-porous materials. Because the sleeves or tubes 44-50 are sealed at the lumen openings 60 of the tip 58, gases and liquids encountered during use of the system 30 within the body are substantially prevented from entering into the sheath 38, except through the tubes 44-50. Accordingly, the internal spaces within the sheath 38 are not exposed to liquids or gases in use.

As noted above, in the embodiments described, the tip 58 is formed of hard or soft plastic or rubber, or similar non-porous materials. In an embodiment, the tip 58 is formed of a transparent plastic, rubber, or polymeric material. In an embodiment, the tip 58 is substantially dome-shaped, and the openings 60 are substantially equally distributed over the tip 58. In the embodiments shown in the Figures (see, e.g., FIG. 10), the tip 58 include an asymmetrical, conical shape in which the openings 60 for the tool lumens are not equally distributed. For example, the opening 60 for one of the tool lumens is located at a point on the tip 58 that is distal of the other openings 60. This orientation provides the ability to have endoscopic tool exit ports that are longitudinally staggered. For example, in an embodiment, the opening 60 for an endoscope tool lumen is located distally of the opening 60 for a second diagnostic or therapeutic endoscopic tool. In this way, the second tool is able to be observed as it exits the tip 58, rather than after it has extended substantially from the tip 58. Other variations are also possible.

For example, turning to FIGS. 15A-H, a number of exemplary embodiments of sheath tips 258 are illustrated. In several embodiments, the tip 258 includes an eccentric taper having an opening 260 for one or more of the tool lumens that is spaced distally from the opening 260 of one or more of the other tool lumens. The taper profile of the tip facilitates advancement of the sheath 38 through, for example, anatomical lumens in a manner comparable to a conventional esophageal dilator. The locations of the openings 260, and the relationships between the locations of the openings 260 and the size of the particular tool lumens, provide additional advantages.

Figure 15A:
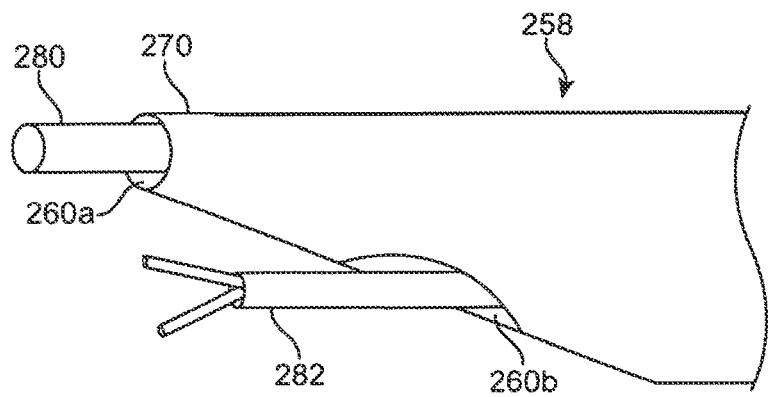
FIG. 15A is a side perspective view of a sheath tip with a distal portion aligned with the tool lumen used by an endoscope.
Figure 15B:
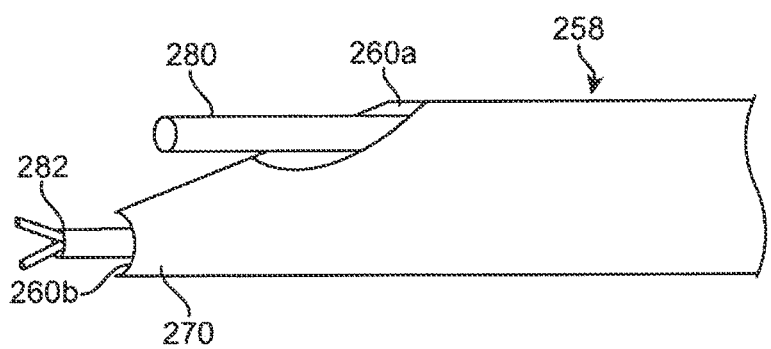
FIG. 15B is a side perspective view of a sheath tip with a distal portion aligned with the tool lumen used by a grasping tool.

In the embodiments shown in FIGS. 15A-B, the tip 258 has an eccentric tapered shape that includes a distal portion 270 of the taper that is aligned with one of the tool lumens extending through the sheath. The distal portion 270 is offset from the longitudinal axis of the sheath 38, creating the eccentric taper. Accordingly, an opening located at the terminal end of the distal portion 270 is located at a point that is distal of the openings for the other tool lumens located on the tip 258. For example, in the embodiment shown in FIG. 15A, the distal portion 270 is aligned with the tool lumen used by an endoscope 280, such that a first opening 260*a* through which the endoscope 280 extends is located distal of a second opening 260*b* through which a grasping tool 282 extends. In the embodiment shown in FIG. 15B, the distal portion 270 is aligned with the tool lumen used by the grasping tool 282, such that the second opening 260*b* is located distal of the first opening 260*a* through which the endoscope 280 extends.

Although not shown in FIGS. 15A-E, additional openings 260*c*, 260*d*, etc. are located on the tip 258 in alignment with respective toot lumens. The offset openings 260*a*, 260*b* provide a tip 258 in which one or more of the tools located in the tool lumens are able to exit the tip 258 through an opening at a longitudinal location different from the other tools. For example, in the FIG. 15A embodiment, the endoscope 280 exits the tip 258 at a location that is distal of the exit port of the grasping toot 282. This allows the user to view the tools through the endoscope 280, while the endoscope 280 is not advanced substantially out of the tip 258. Other perspectives are provided by locating the openings 260*a-d* at desired locations.

Figure 15C:
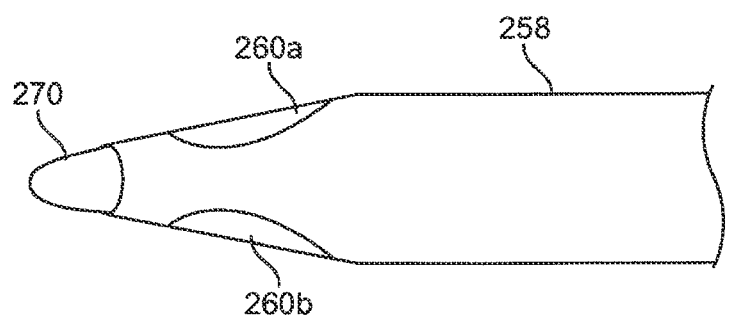
FIG. 15C is a side perspective view of a sheath tip having a taper on the distal portion located generally along the longitudinal axis of the sheath, and the openings located proximally of the distal portion of the tip.

In the tip embodiment shown in FIG. 15C, the taper on the distal portion 270 is located generally along the longitudinal axis of the sheath 38, and the openings 260*a*, 260*b* are located proximally of the distal portion 270 of the tip 258.

As with the embodiments described above, additional openings 260c, 260d, etc. may be included on the tip, but are not shown in FIG. 15C.

Figure 15D:
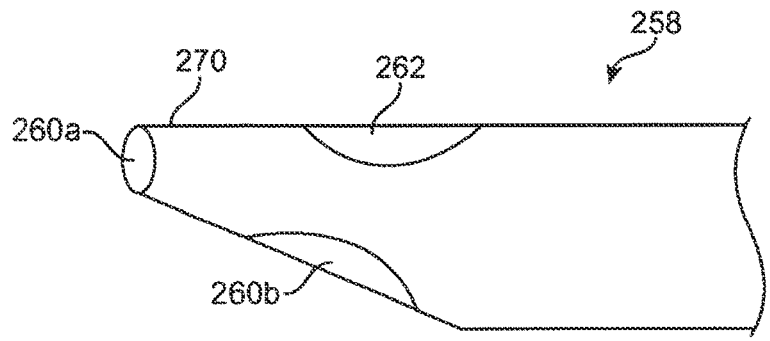
FIG. 15D is a side perspective view of a sheath tip with a secondary exit port oriented to position a tool radially off-axis from the longitudinal axis of the tool lumen through which the endoscope extends.
Figure 15E:
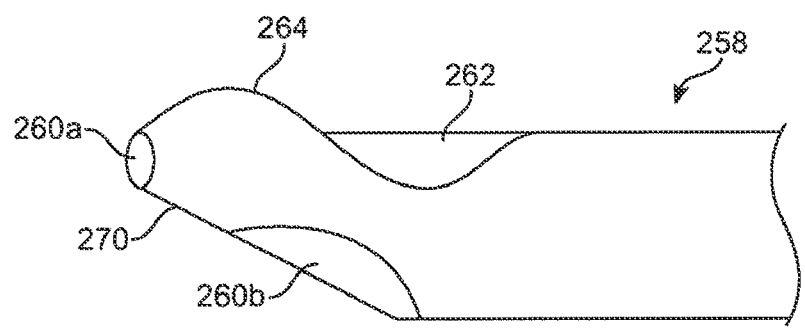
FIG. 15E is a side perspective view of a sheath tip having a raised portion at the distal edge of the secondary exit port to provide additional support for an endoscope or other tool.

In FIGS. 15D-E, additional tip embodiments are shown. In these embodiments, the tip 258 includes a secondary exit port 262 located proximally of the first opening 260a and in communication with the tool lumen corresponding with the first opening 260a. The secondary exit port 262 provides an optional opening through which a tool, such as an endoscope 280, is able to exit the tip 258. In other embodiments, tools other than an endoscope 280, such as a grasping tool 282 or others, are advanced through the secondary exit port 262. In the embodiments shown in FIGS. 15D-E, the secondary exit port 262 is oriented such that, when the endoscope 280 or other tool extends through the secondary exit port 262, the endoscope 280 or other tool extends radially off-axis from the longitudinal axis of the tool lumen through which the endoscope 280 extends. Accordingly when the endoscope 280 is routed through the secondary exit port 262, the endoscope 280 provides an alternative viewing angle to the user of the distal portion of the tip 258 and of the tools exiting through the other openings 260b-d provided on the tip 258. In the embodiment shown in FIG. 15E, a raised portion 264 is provided at the distal edge of the secondary exit port 262. The raised portion 264 provides additional support for an endoscope 280 or other tool extending through the secondary exit port 262, thereby guiding the endoscope 280 or other tool to an off-axis extension through the exit port 262.

The tip embodiments shown in FIGS. 15D-E provide the user with the option of viewing through the endoscope 280 as it extends either from the first opening 260a, generally aligned with the tool lumen through which the endoscope 280 extends, or as the endoscope 280 extends through the secondary exit port 262 to an off-axis position. In an embodiment, the endoscope 280 includes a steerable distal portion that is used to guide the endoscope through the secondary exit port 262. In either case, the endoscope 280 is routed through the first opening 260a or through the secondary exit port 262 and may be steered, rotated, retroflexed, or otherwise manipulated by the user to obtain a desired position for viewing. As noted previously in other embodiments, additional tools other than the endoscope 280 are able to be routed through the secondary exit port 262.

Figure 15F:
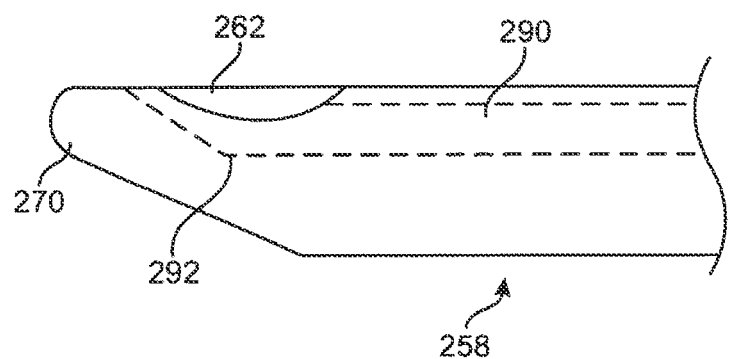
FIG. 15F is a side perspective view of a sheath tip having an eccentric taper terminating in a distal portion.

In the embodiment shown in FIG. 15F: the tip 258 includes an eccentric taper terminating in a distal portion 270, as described above in relation to the embodiments show in FIGS. 15A-B and 15D-E. In the FIG. 15F embodiment, however, the tip 258 includes only a secondary exit port 262 in communication with the tool lumen 290, and does not include a first opening 260a. Advantageously, the distal end of the tool lumen 290 includes a slope 292 that guides an endoscope 280 or other tool toward the secondary exit port 262. Accordingly, the endoscope 280 or other tool located in the tool lumen 290 is routed to the off-axis extension provided by the secondary exit port 262.

Figure 15G:
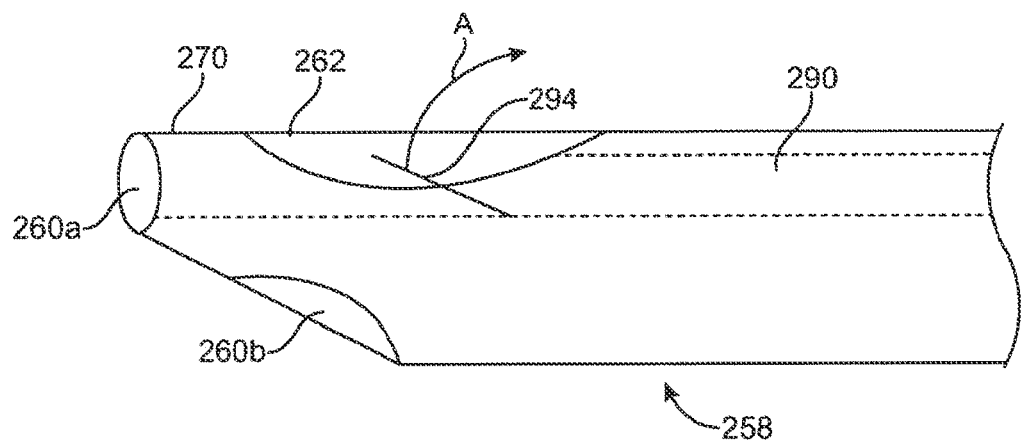
FIG. 15G is a side perspective view of a sheath tip similar to the sheath tip shown in FIG. 15D and also including an activatable ramp.

The tip embodiment shown in FIG. 15G is essentially identical to the embodiment described above in relation to FIG. 15D, but also includes an activatable ramp 294. The ramp 294 is controlled by a push rod, pull wire, or other mechanism that is operably coupled to an actuator located, for example, on the handle of the device, The ramp 294, under control of the user, is selectively movable in the direction of the arrow "A" to an upright position, illustrated in FIG. 15G, in which the ramp 294 provides a slope or guide that routes an endoscope 280 or other tool located in the lumen 290 to extend through the secondary exit port 262 as the endoscope 280 or other tool is advanced through the lumen 290. The ramp 294 is also movable to a flat position in which the ramp 294 extends flat against the inner wall of the lumen 290, to allow the endoscope 280 or other tool to extend through the first opening 260a.

Figure 15H:
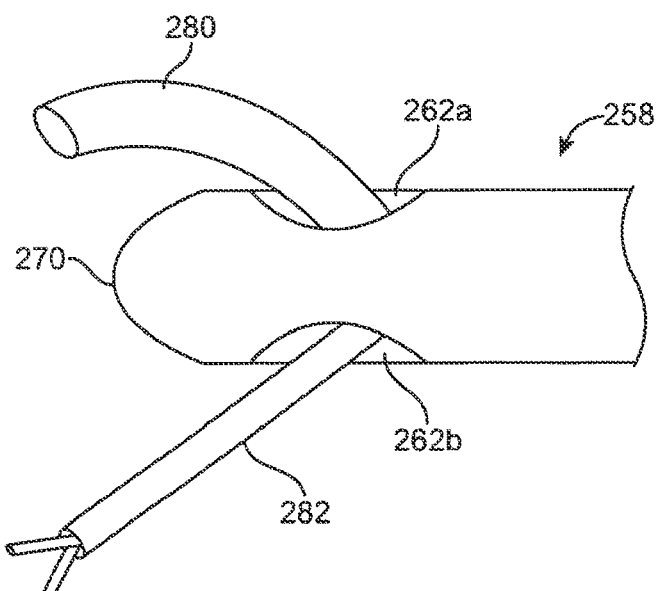
FIG. 15H is a side perspective view of a sheath tip having a pair of secondary exit ports located proximally of the distal portion of the tip.

Turning to FIG. 15H, another embodiment of a tip 258 includes a pair of secondary exit ports 262 a, 262 b located proximally of the distal portion 270 of the tip. In the embodiment shown, the distal region 270 includes a rounded distal tip. An endoscope 280 extends through the first secondary exit port 262 a, and a grasping tool 282 extends through the second secondary exit port 262 b. In an embodiment, each of the endoscope 280 and the grasping tool 282 includes a steerable distal portion that provides the user with the ability to extend the endoscope 280 and grasping tool 282 through the respective secondary exit ports 262 a, 262 b and to guide the tools to the desired locations.

As noted previously, in each of the tip embodiments described, the tip 258 is formed of a material having desired material properties. In some embodiments, the tip 258 is formed of a hard or soft plastic or rubber, or similar non-porous materials. In some embodiments, the tip 258 is formed of a transparent plastic, rubber, or polymeric material. A transparent tip 258 provides the user with the ability to use an endoscope 280 located in a first tool lumen to more easily view a grasping tool 282 or other tool located in an adjacent lumen. In addition, with the transparent tip 258, the distal portion 270 of the tip 258 may be placed flush against tissue with an endoscope 280 pulled slightly proximal of the distal end to visualize tissue without "whiting out" or "pinking out" as commonly occurs during endoscopic procedures. The transparent tip 258 also provides the ability to direct light from an endoscope 280 radially through the tip 258 to illuminate areas that are otherwise not subject to illumination with a non-transparent tip.

Referring once again to FIGS. 4, 5, and 10, the tubes 44-50 extend proximally within the sheath 38 from the tip 58 to the handle 36. As shown in FIG. 5, the proximal ends of the tubes 44-50 are initially free, i.e., unattached to the handle 36. The tubes 44-50 each have a lumen end fitting 134 used to attach the proximal ends of the tubes to a lumen block 130 on the handle 36.

In an embodiment, the steering wires 80 and coils 82, or other tension or compression steering elements used, extend proximally through the sheath 38 to steering control knobs 140 and 144, as shown in FIG. 5. In the illustrated embodiments, four steering wires or elements 80 are used. The first and third wires, oriented on opposite sides of the first link 74, are connected on a shaft or spool joined to the first control knob 140, for example, to provide vertical or up/down steering movement to the steerable section 42. Similarly, second and fourth steering wires or elements 80 are attached to a shaft or spool joined to the second steering control 144, to provide lateral or left/right steering movement to the steerable section 42. In the illustrated embodiment, steering brake or locking controls 142 and 146 are associated with each steering control 140 and 144.

In the embodiments shown, the sheath 38, which includes or contains the tip 58, steering section 42, tubes 44-50 and steering elements, is attached to the handle 36 during manufacture.

FIGS. 7A-B and 8A-B show two embodiments of a shapelock assembly 34. A first embodiment, shown in FIG. 7A and BA, includes a locking handle 172 that opens at its distal end, whereas the second embodiment (FIGS. 78 and 8B) includes a locking handle 172 that opens at is proximal end. With the exception of the locking handle orientation, the illustrated embodiments are functionally identical. In some embodiments, the shapelock assembly 34 is reusable. In the examples shown in FIGS. 7A-B and 7A-B, the shape lock body 150 is formed by segments, such as links 156 that are pivotably attached to (or positioned next to) each other in a nested arrangement. In an embodiment, the links 156 are formed as nested rings, so that the shapelock body 150 is tubular, or has an open internal through passageway. Lock wires 158 extend from a base 160 to the distal end 178 of the shapelock body 150.

Figure 7A:
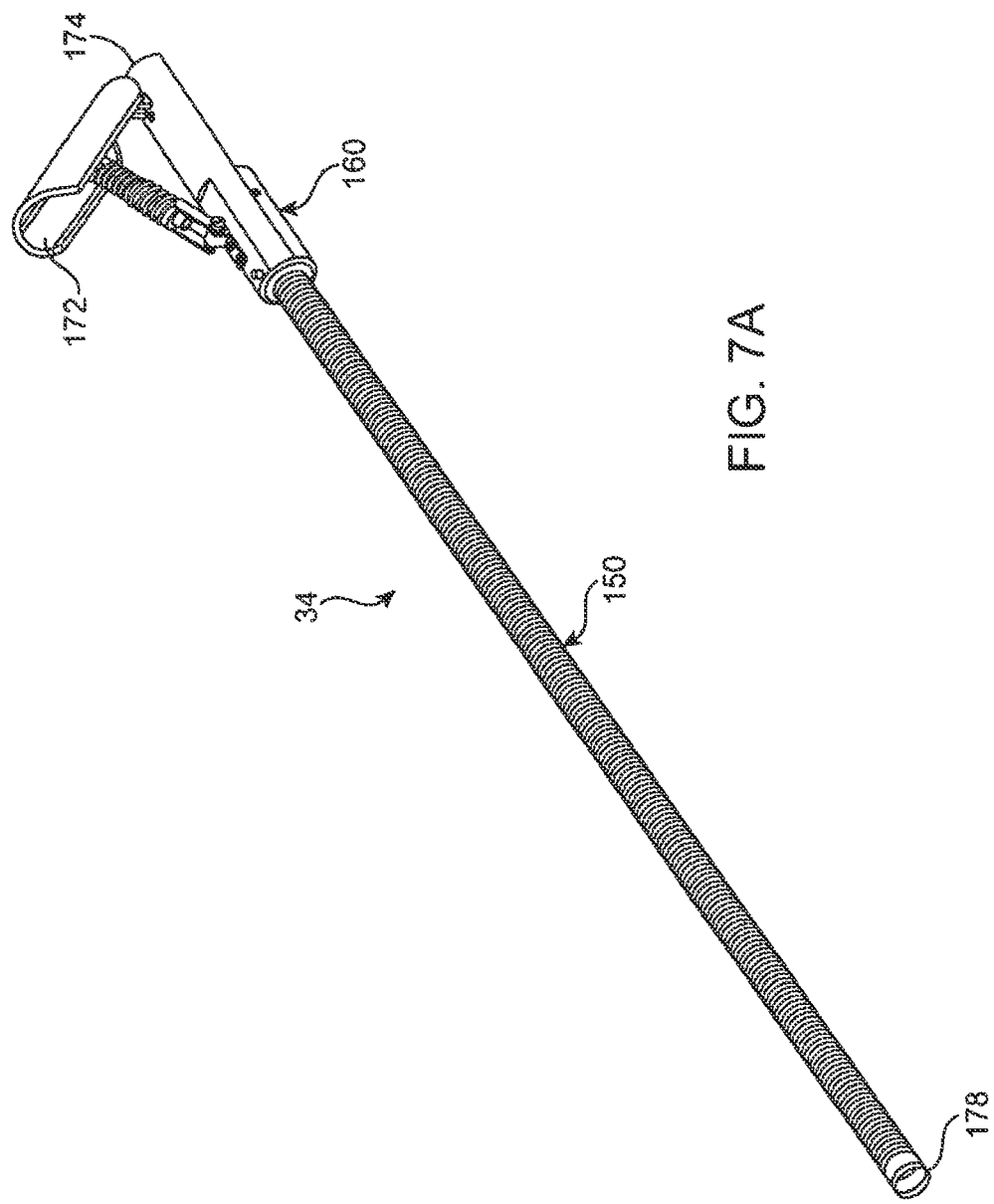
FIG. 7A is a front, top, and left side perspective view of a first embodiment of a shapelock assembly.
Figure 7B:
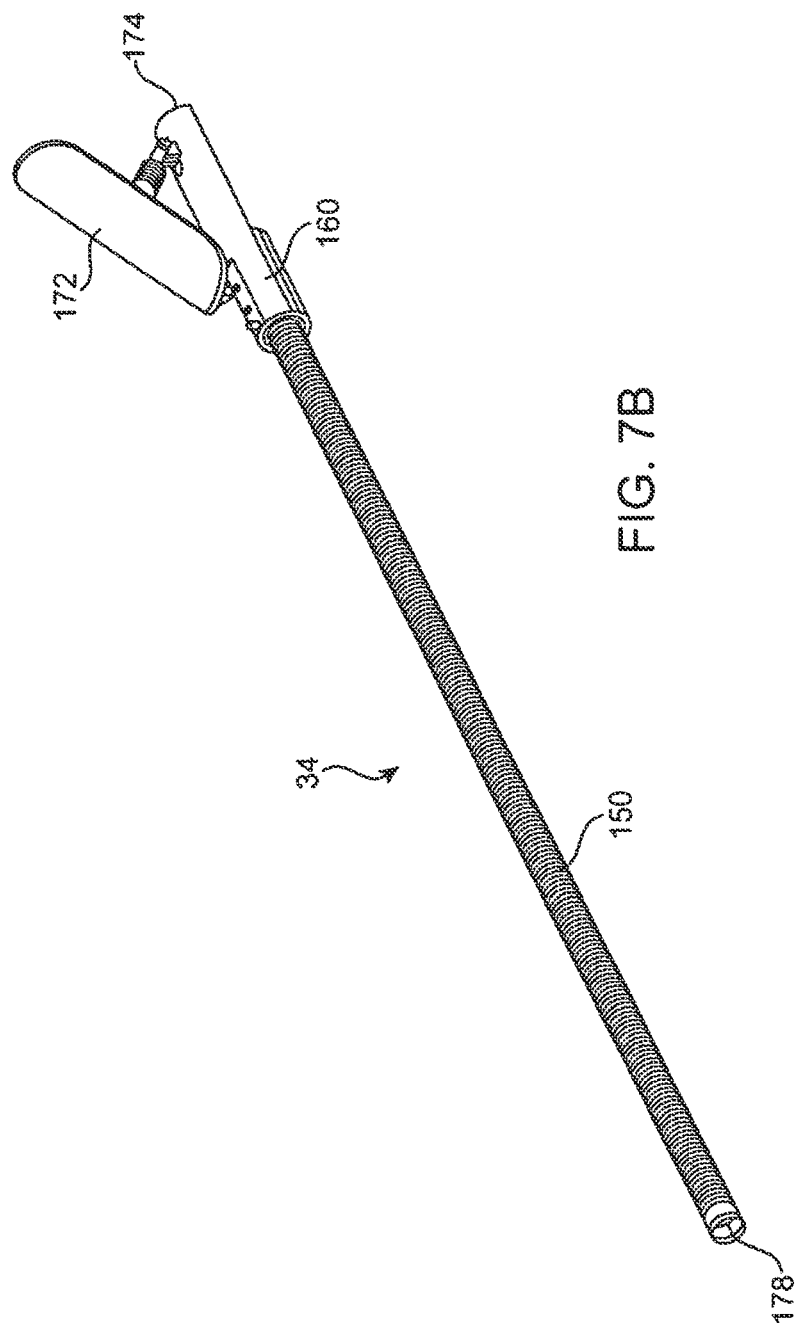
FIG. 7B is a front, top, and left side perspective view of a second embodiment of a shapelock assembly.
Figure 8A:
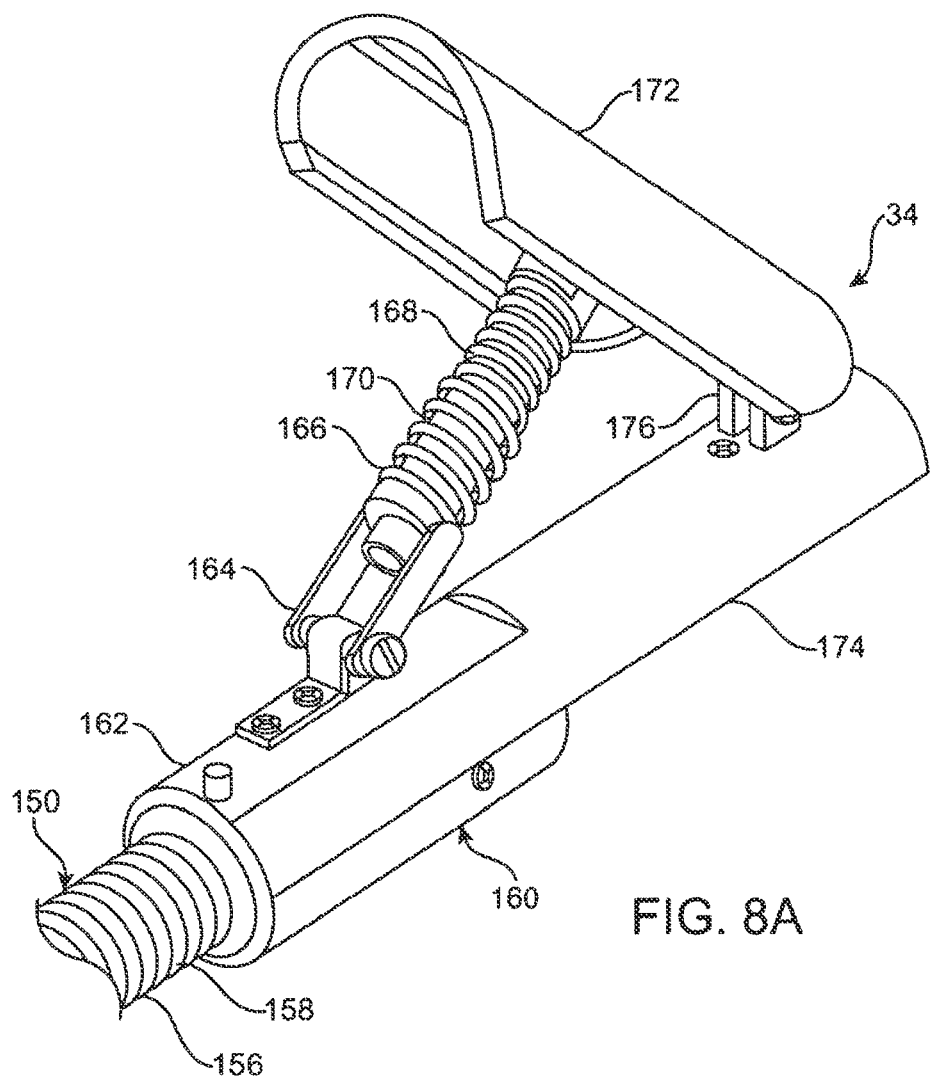
FIG. 8A is an enlarged front, top, and left side perspective view of the back end of the shapelock assembly shown in FIG. 7A.

As shown in FIGS. 8A-B, the lock wires 158 pass through a compression collar 162 in the base 160. In the FIG. 8A embodiment, the proximal end of the locking handle 172 is supported on a handle pivot block 176 on a base extension 174. In the FIG. 8B embodiment, the distal end of the locking handle 172 is supported on the handle pivot block 176. A spring shaft 170 is pivotably attached to the locking handle 172 at a position spaced apart from the pivot block 176. Springs 166 and 168 are supported on a clevis 164 and positioned around the spring shaft 170. Pushing or squeezing the locking handle 172 down toward the base 160 causes the compression collar 162 to compress the nested links 156 against one another over the fixed-length lock wires 158. This causes the shape lock body 150 to become substantially rigid. With the handle in the open position as shown in FIGS. 7A-B and 7A-B, compression of the links 156 on the lock wires 158 is released, and the shape lock body 150 is generally flexible. The first spring 166 has a lower spring constant than the second spring 168. This allows for easier initial downward pivoting movement of the lock handle 172, with relatively lower force. As the locking handle 172 moves down toward the base 160, where the user's hand has greater mechanical advantage, the second stiffer spring 168 applies proportionally increasing force to the compression collar 162. In an alternative embodiment, a single spring is used and the biasing force is provided by only the single spring through the entire travel of the locking handle 172.

The shapelock assembly 34 embodiments shown in FIGS. 7A-B and 8A-B are examples of various shapelocking assemblies that are suitable for use in the endoscopic system 30. The specific shapelock assembly mechanism used is not essential, so that a large number of alternative mechanisms that can transition from substantially flexible to substantially rigid may be used. Examples of alternative shapelock assembly mechanisms suitable for use in the endoscopic system are described, for example, in U.S. Pat. Nos. 6,783,491 and 6,960,163, and United States Patent Application Publication No. US 2006/005852, each of which is incorporated by reference herein. These patents and publications also provide additional details about the structure and operation of the shapelocking assemblies described herein.

In an embodiment, the links 156 and other elements forming the shapelock body 150 advantageously have high strength and yet are light weight. The locking mechanism associated with the shapelock body typically is also advantageously highly reliable. In some embodiments, the shapelock assembly 34 portion of the endoscopic system 30 is relatively more costly to construct (in terms of labor, time, and/or expense) than is the disposable assembly 32. Moreover, in some embodiments, it is relatively more simple, efficient, and/or cost-effective to clean and/or re-sterilize the shapelock assembly 34 portion of the endoscopic system 30 alone or independently of the disposable assembly 32. For example, in some embodiments, the disposable assembly 32 includes rubber coatings, steering links, lumens, and/or other components that are less easily, efficiently, or effectively cleaned and/or sterilized. Accordingly, there are significant advantages in being able to reuse the shapelock assembly 34 over multiple procedures and/or with multiple patients, and to dispose of the disposable assembly 32 after a single or limited number of patient uses.

Figure 6A:
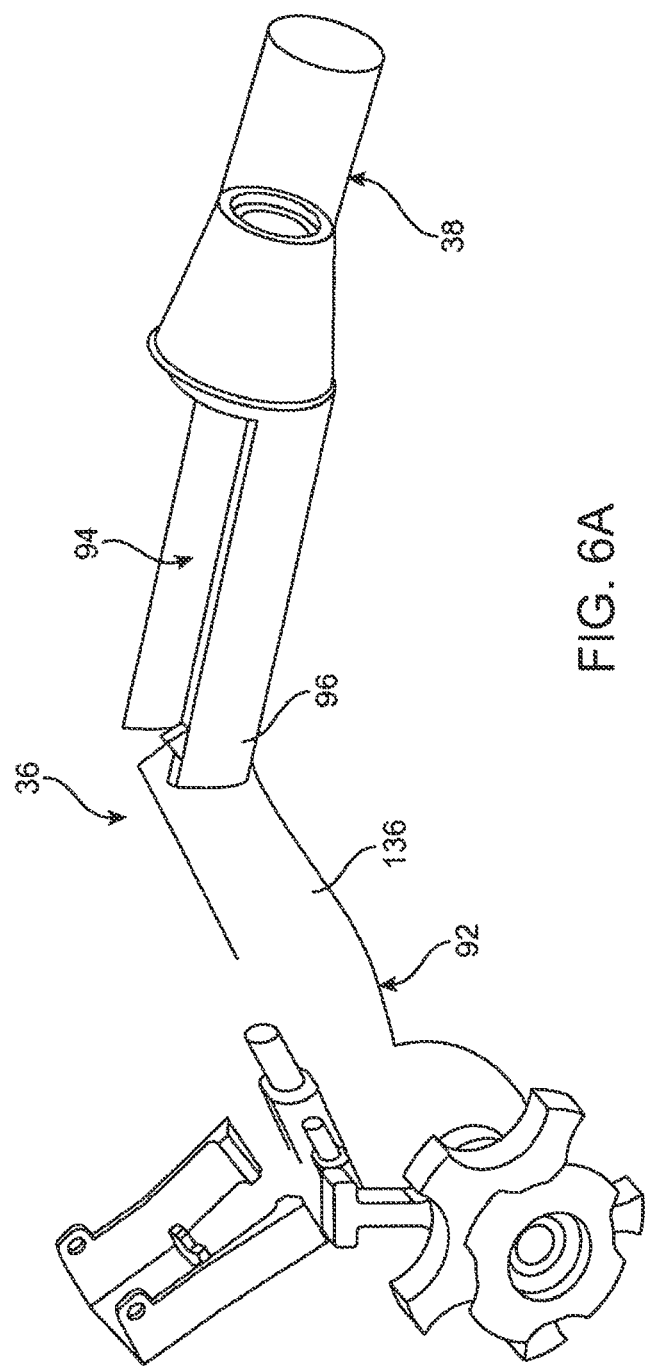
FIG. 6A is a front, top, and right side perspective view of the handle shown in FIGS. 4 and 5, and illustrating the hinge connecting the handle barrel to the handle base.
Figure 6B:
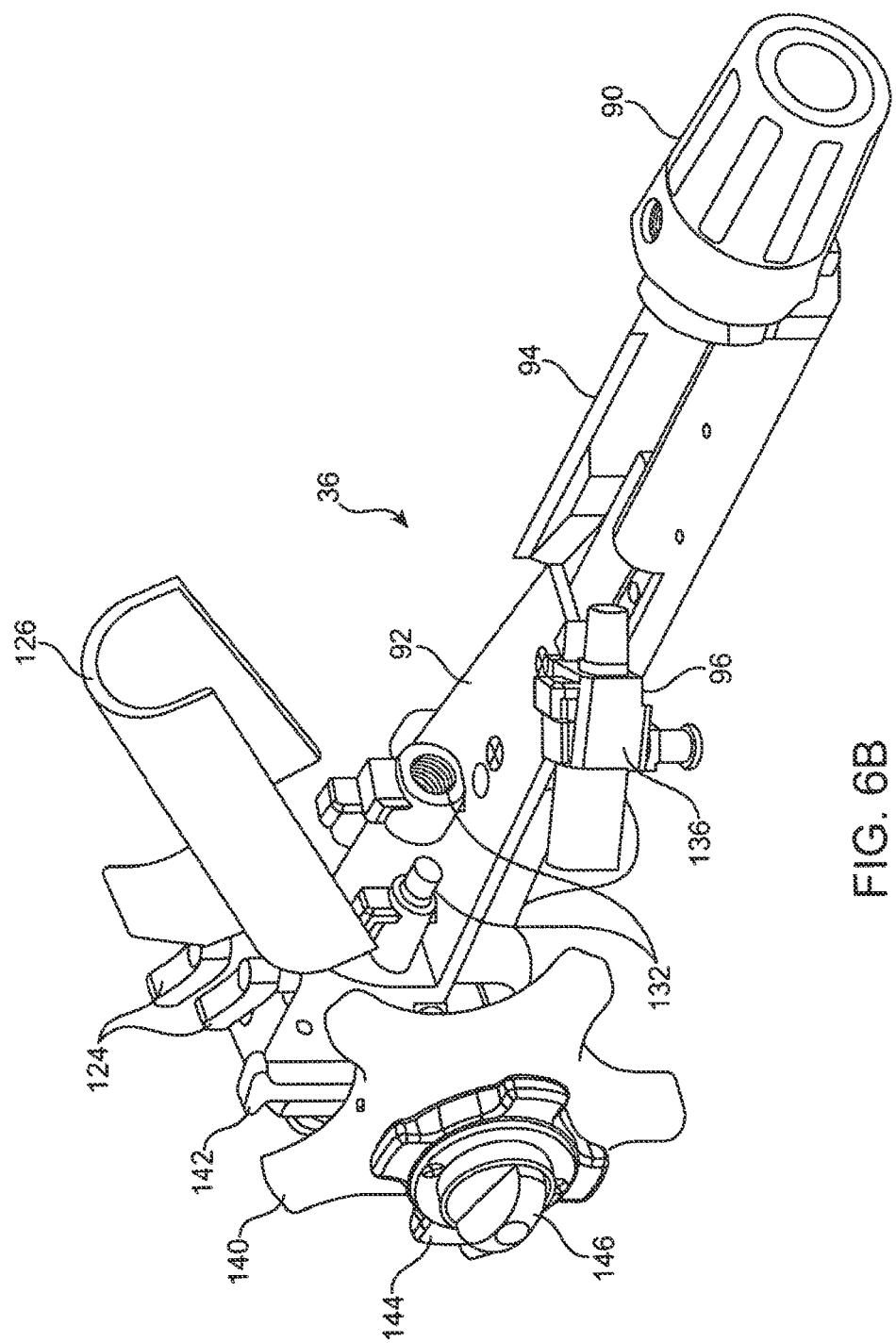
FIG. 6B is a front perspective view of another embodiment of a handle portion of an endoscopic system.
Figure 6C:
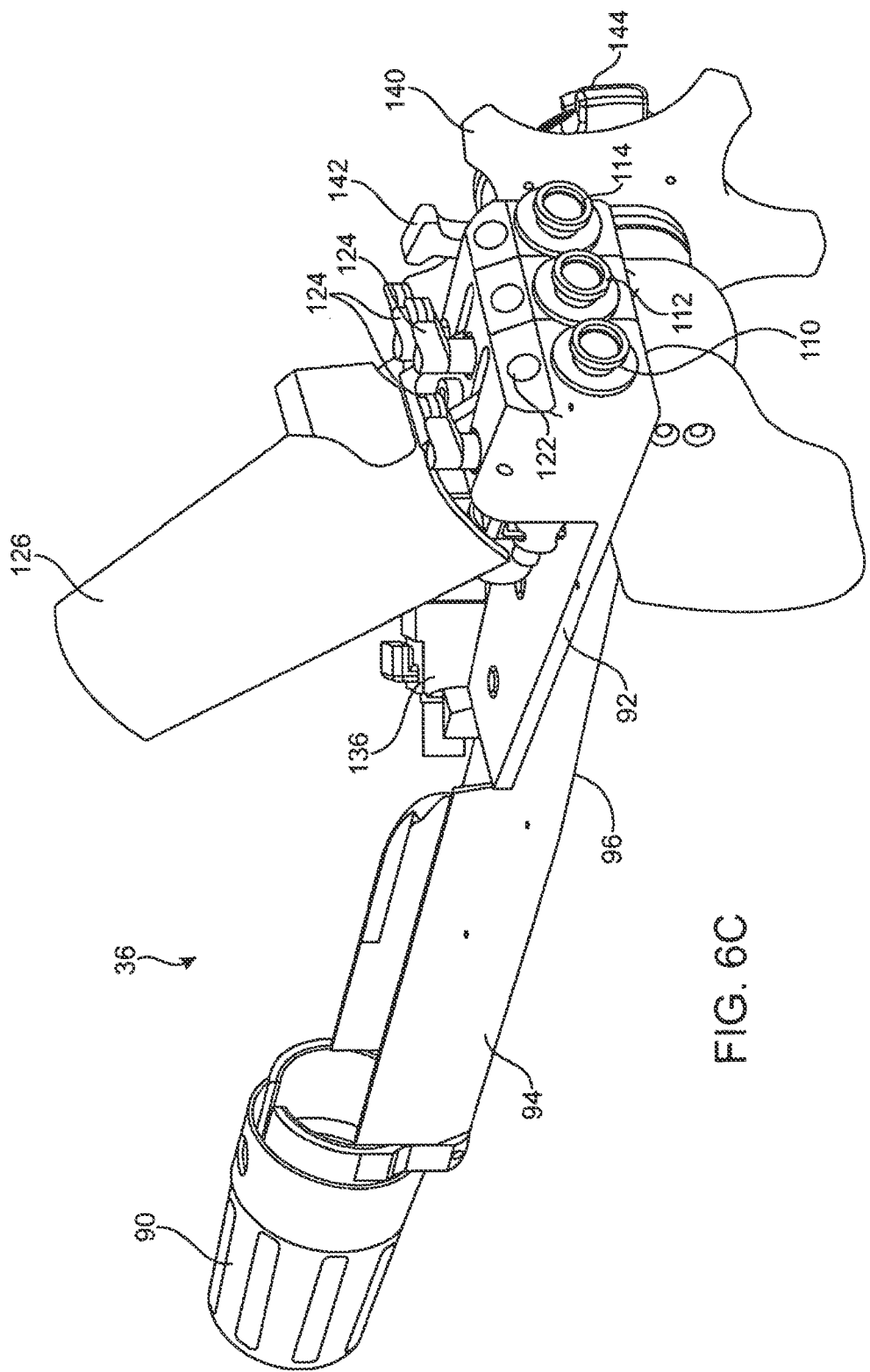
FIG. 6C is a back perspective view of the embodiment of FIG. 6B.

In an embodiment, the disposable assembly 32, which includes the handle 36, and sheath 38, is provided in a sterile condition, for example, within a sterile package. To prepare for use, e g., in an operating room, the assembly 32 is removed from the sterile package, in the form as shown in FIG. 5. The sleeves or tubes 44-50 are loose or unattached at their proximal ends. The handle barrel 94 is pivoted downwardly relative to the handle base 92 about the hinge 9, as shown in the embodiment illustrated in FIG. 6A. FIGS. 6B-C show another embodiment of the handle 36 in its locked position, without being pivoted about the hinge 96. The shapelock assembly 34 is then installed into the disposable assembly 32 as follows. The shapelock assembly 34 is removed from its sterile package, if any. With both the handle/sheath assembly 32 and the shapelock assembly 34 in a sterile field (for example on a sterile sheet on an operating room cart or table), the proximal ends of the tubes 44-50 are threaded into the open distal end 178 of the shapelock assembly 34. The shapelock assembly 34 may be in a rigid or in a flexible condition. The body 150 of the shapelock assembly is advanced into the sheath 38 until the distal end 178 of the shapelock body 150 is adjacent to the steerable section 42, at position 180 shown in FIG. 9. Once the shapelock assembly 34 is moved into this position, the tubes 44-50 extend out from the proximal end of the shape lock body 150, beneath the base extension 174, as shown in FIG. 3.

During installation of the shapelock assembly 34 into the disposable assembly 32; the cover 126 on the handle 36 is in the up or open position. The proximal end of each tube 44-50 is then connected to a respective fitting 132 on the lumen block 130 on the handle 36. Referring to FIG. 4, the tube fittings 134 on the tubes are clamped in place via lumen clamps 132. Lumen bores 148 extend from the distal end of the lumen block 130, where the tubes 44-50 are attached, to lumen entry guides 110, 112, and 114 on the proximal end of the handle 36, as shown in FIG. 2. A tether 118 holds a cap 116 containing a cap seal 120 on each of the lumen entry guides 110-114. A Luer port 122 connects into each lumen bore in the lumen block 130, distally of the lumen entry guides 110-114.

With the shapelock assembly 34 installed and the tubes 44-50 connected to the handle 36, the handle barrel 94 is pivoted back to the closed position as shown in FIG. 4. The cover 126 is closed and may be locked by turning a cover lock knob 128, as shown in FIGS. 2 and 5. The flat bottom side of the base extension 174 of the shapelock assembly 34 is supported on a flat raised surface in the handle 36, to keep the shapelock assembly 34 stabilized relative to the handle 36.

One or more endoscopic tools may be inserted into and through the system 30 via the entry guides 110-114, with the distal ends of the tools moved through the sleeves or tubes 44-50 to the tip 58. In the embodiment shown, the cap seals 120 seal against the shafts of the tools. This prevents extensive leaking of insufflation air or gas. In other embodiments, seals are provided at other locations along the tool lumens, such as within the handle 36, at an intermediate portion in the sheath 38, and/or at or near the distal ends of the tool lumens near the tip 58. In an embodiment, thumb screws 124 on the handle 36 are tightened to prevent sliding front/back movement of the tools within the lumens. In an embodiment, one or more of the Luer ports 122 are connected to a gas/insufflation source, a liquid source, or a vacuum source. Referring to FIGS. 2 and 5, the proximal ends of the tubes 44-50 in the handle 36, and the lumen bores in the lumen block 130 are substantially straight. This allows endoscopic tools to be moved into the system 30 easily, since the endoscopic tools move in a substantially straight path when installed into the system 30.

Referring to FIGS. 1 and 5, in an embodiment, a side access fitting 136 is provided on the side of the handle 36, with one of the tubes 44-50 connecting into a side lumen entry guide 138. The side access fitting 136 allows one or more endoscopic tools to be positioned off to the side of the handle 36, away from the position of the other endoscopic tools extending out from the back of the handle. The side access fitting 136 is preferably oriented at an angle of 5-90 degrees or more, and more preferably 15-60 degrees, relative to the longitudinal axis of the sheath 38. This allows one user to use, e.g. an endoscope routed through the side access fitting 136, while a second user operates other tools routed through the other lumens, with each user having more room around the handle 36.

The tip 58 and sheath 38 are then moved into the patient. For diagnostic, therapeutic, or surgical procedures in the gastrointestinal (GI) tract, the sheath 38 is inserted into the mouth and throat and guided through the esophagus to the stomach or other location. For procedures involving the large intestine or colon, the sheath is guided through the anus and rectum. In an embodiment, a hydrophilic coating is applied to the outside surface of the sheath 38 to allow the sheath to slide more easily through body openings. In other embodiments, the sheath 38 is provided with a coating that includes one or more of a bactericide, a pain reducer, a relaxant, and/or another facilitating or therapeutic material suitable for use as a coating over the sheath.

To maneuver within these or other hollow body organs or to position the tip 58 for a specific procedure, the steering controls 140 and 144 are used to steer the steerable section 42. To better hold the sheath 38 into a desired position or shape, the shapelock assembly 34 may be made rigid by pressing the lock handle 172 down, from the position shown in FIGS. 1 and 2, to the position shown in FIG. 4. This places the shapelock assembly 34 into a substantially rigid condition, which correspondingly locks the sheath 38 surrounding the shape lock 34 into the same shape or position.

Figure 12:
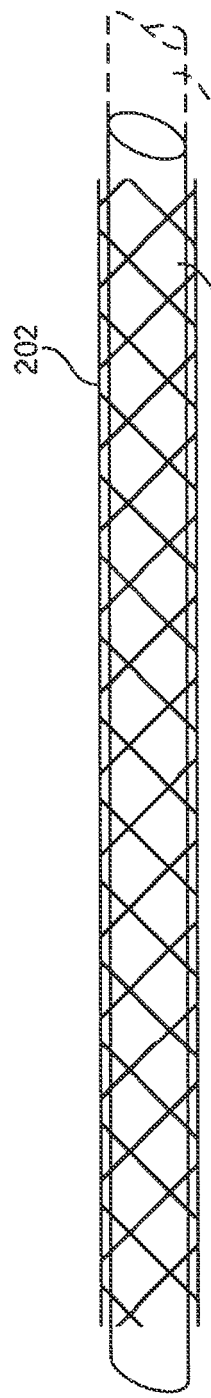
FIG. 12 is a schematically illustrated side view diagramming a first step in manufacturing the sheath shown in FIG. 9.
Figure 13:
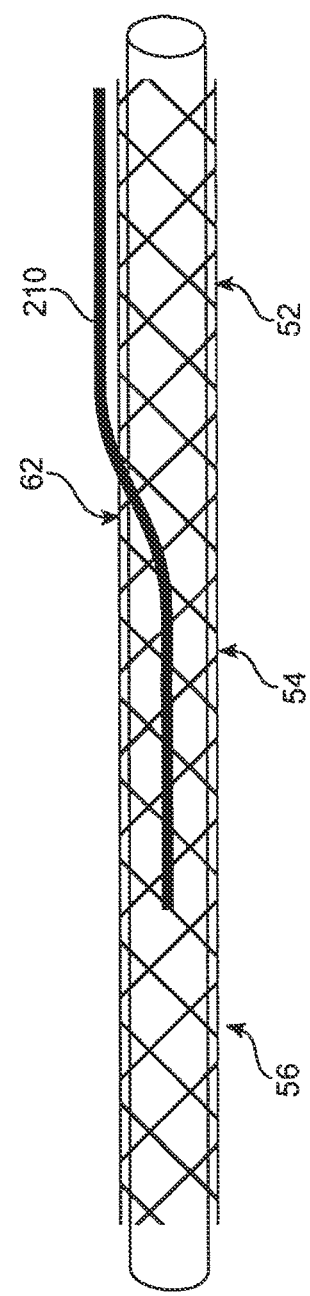
FIG. 13 is a schematically illustrated side view showing a second step in manufacturing the sheath shown in FIG. 9.
Figure 14:
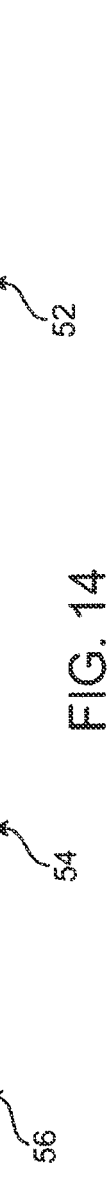
FIG. 14 is a schematically illustrated side view showing a subsequent step in the manufacture of the sheath shown in FIG. 9.

FIGS. 12-14 show an example of a method of manufacturing a sheath 38 suitable for use in the disposable assembly 32 embodiments described herein. A first or inner layer 200 of a braid or woven mesh of a reinforcement material is placed onto a mandrel 201, as shown in FIG. 12. In an embodiment, the mandrel 201 is a cylindrical rod (e.g., aluminum) having a thin polymeric (e.g., polyolefin shrink tube) coating. In an embodiment, the reinforcement material is a mesh formed of a polymeric material such as polyethylene terephthalate (PET) or other suitable reinforcement material. A second layer 202 of reinforcement material is then applied over the first layer 200. The second layer 202 of reinforcement material will extend over the entire length of the sheath 38, so a sufficient length of the material is placed on the mandrel 201. The first or inner layer 200 of reinforcement material is shorter than the second layer 202, extending from the proximal end of the sheath 38 and terminating at the steerable section 42. Passageway forming wires 210 are then temporarily installed. Each wire 210 will form a passageway in the sheath for a steering coil and wire. The forming wires have a diameter nominally larger than the steering coils 82. If the sheath will have four steering wires, then four forming wires 210 are installed, equally radially spaced apart (i.e., at 90 degree intervals around the circumference). The passageway forming wires 210 are installed between the first layer 200 and the second layer 202 of reinforcement material, and are installed only in the section of the sheath 38 that the first layer 200 and second layer 202 overlap. In an embodiment, the forming wires 210 are stainless steel wires coated with polytetrafluoroethylene to facilitate removal of the wires from the sheath after the skin layer 204 is formed, as described below.

In other embodiments, the order of installation of the first layer 200 of reinforcement material, the second layer 202 of reinforcement material, and the passageway forming wires 210 are different. For example, in an embodiment, the passageway forming wires 210 are installed after the first layer 200 is installed, but before the second layer 202 is installed. A person of ordinary skill in the art will recognize that other orderings are also possible.

Once the first layer 200 of reinforcement material, second layer 202 of reinforcement material, and passageway forming wires 210 are installed as described above, a skin layer 204 is applied over the first and second layers. The skin layer 204 is formed of a flexible material that is capable of providing the performance capabilities desired for the sheath 38. In an embodiment, the skin layer 204 is formed of a polymeric material such as plastisol that is applied using a dipping and/or spinning process. The skin layer 204 is applied over the section of overlap of the first layer 200 and second layer 202, and over the remainder of the second layer 202 that is not overlapping the first layer 200. After drying or curing the skin layer 204, the forming wires 210 are pulled out or otherwise removed. This leaves passageways 212 for the steering wires within the walls of the sheath 38, as shown in FIG. 11A. Specifically, each passageway 212 is located within the skin material and in between the first and second layers of braid or reinforcement material. In an embodiment, the passageways 212 are formed in straight, radially spaced alignment extending over the proximal length of the sheath 38. In other embodiments, the passageways 212 include partial spiral sections that are provided in order to locate the proximal and distal exit points of the steering wires 80 from the sheath 38 as desired.

In alternative embodiments, the passageways 212 are formed having a non-circular cross-sectional shape. For example, as shown in the embodiment illustrated in FIG. 11B, four passageways 212 are formed having an elongated cross-sectional shape extending over a portion of the circumference of the sheath 38. In an embodiment, the elongated cross-sectional shape of the passageways 212 is obtained by using a plurality of forming wires 210 placed adjacent to one another prior to applying the skin layer 204, to form each such passageway 212. The elongated passageways 212 provide space in which the coils 82 are able to bend and flex without impairing the flexibility of the sheath 38. In addition, in an embodiment, each of the coils 82 is attached to the sheath 38 at both the proximal and distal ends of the coil. In other embodiments, only one end (e.g., proximal or distal) of the coil 82 is attached to the sheath 38, while the other end of the coil 82 is allowed to float within the passageway 212 in order to enhance the flexibility of the sheath 38.

Referring to FIGS. 9 and 11 at position 180, the steering wires 80 exit from the passageways 212, run inside of the steerable section 42, and attach to the front segment of the steerable section 42. Referring to FIG. 9, distally of position 180, the sheath includes a single layer of reinforcement and skin. Toward the proximal end of the sheath 38, the steering wires are contained within the passageways 212 and extend to the handle 36, where the steering wires 80 are operably connected to the control knobs 140 and 144. Consequently, the shape lock 34 may be inserted into the central sheath opening 220 without contacting or interfering with the steering wires.

In other embodiments, the layers of reinforcement material 200 and 202 are tubes of metal or plastic with a braided or woven structure. More or fewer reinforcement layers may be included over either a portion or the full length of the sheath 38 in order to change the stiffness, torque transmission capabilities, strength, or other material properties of the sheath 38. In other embodiments, various materials may be used for the skin, including other polymers applied by dipping, spinning, or extruding processes. Since the reinforcement materials will generally have an open structure, some skin material may pass through it to the mandrel, tending to create a smooth inside wall surface. In other embodiments, the reinforcement materials substantially prevent the skin material from penetrating, such that the first layer 200 of reinforcement material is partially or fully exposed on the interior surface of the sheath 38. The materials, construction, and design details of the sheath may be varied, provided that the sheath is substantially flexible and substantially prevents the shapelock from coming into contact with body fluids.

Although the endoscopic system embodiments described above include a reusable portion that includes a shapelock assembly, other embodiments include other components. For example, in some embodiments the sheath has sufficient strength and stiffness to allow it to be used without a shapelock assembly. In those embodiments, a non-shape-locking core or skeleton member (either rigid or flexible), a stiffening spring, a coil, a tube, or a rod is placed into the central opening 220 of the sheath, instead of the shapelock assembly. In other embodiments, the sheath and handle assembly are used with no additional support component. In addition, although the embodiments described include a plurality of guide way members defining tool lumens, in other embodiments the guide way members define only a single lumen, or two or more lumens.

Figure 16:
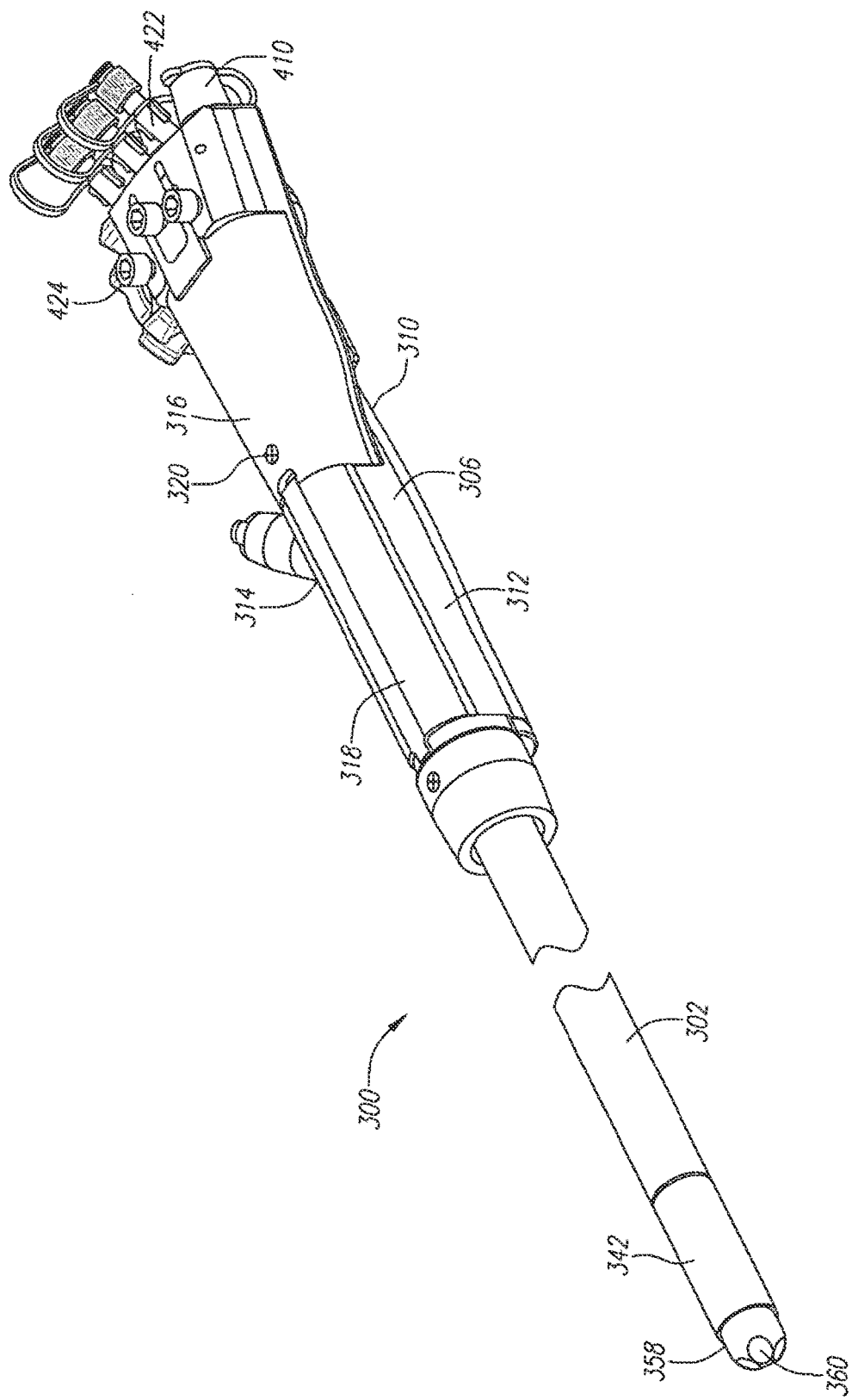
FIG. 16 is a perspective view of an alternative embodiment of an endoscopic system.

An alternative embodiment of an endoscopic system that does not include a shape-locking assembly is shown in FIG. 16. In the embodiment, the endoscopic system 300 includes a flexible shaft 302 attached to a handle 306. The shaft 302 includes a tip 358 attached to the distal end of a steerable section 342. In the embodiment shown, the tip 358 is substantially dome-shaped, having a plurality of openings 360 providing access to the tool lumens. The tip 358 is formed of a relatively soft elastomeric material, such as plastic, rubber, or other polymer.

The handle 306 includes a housing 310 that includes a lower portion 312 and an upper portion 314. The upper portion 314 of the housing includes a manifold cover 316 and a lumen cover 318. In the embodiment shown, there is no shapelock assembly or other removable skeleton member that is removably inserted into and through the shaft 302. Accordingly, the manifold cover 316 and lumen cover 318 are fixed to the handle by an attachment member such as a screw 320. The manifold cover 316 and lumen cover 318 provide a protective covering for the tubes 344-350 (see FIGS. 17A-B) that extend through the shaft 302 and connect at their proximal ends to a tool manifold 430.

Figure 17B:
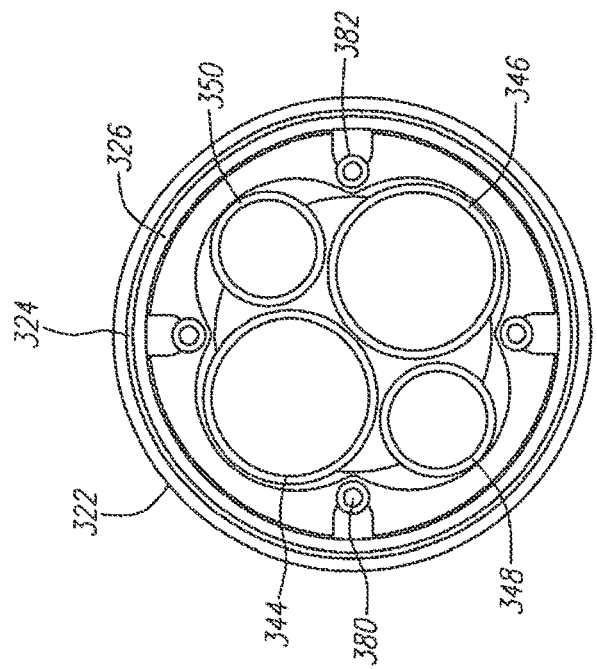
FIG. 17B is a second cross-sectional view of the shaft of the endoscopic system of FIG. 16.
Figure 17A:
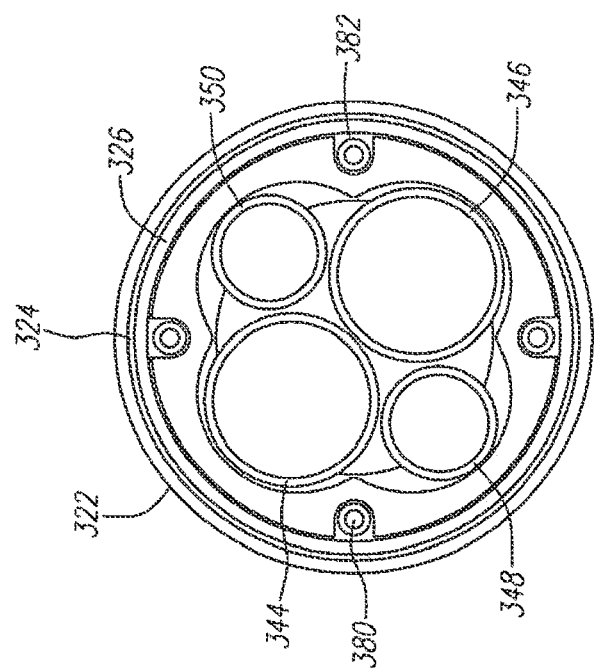
FIG. 17A is a cross-sectional view of the shaft of the endoscopic system of FIG. 16.

Turning to FIGS. 17A and 17B, cross-section views of the shaft 302 of the alternative endoscopic system 300 embodiment are shown. The shaft 302 has a composite construction, including an outer layer 322, a body member 324, and an inner layer 326. The composite construction provides the shaft with improved strength, flexibility, and torque transmission capability over conventional endoscopic shaft constructions. In the embodiment shown, the outer layer 322 and inner layer 326 each include one, two, three, or more layers of a braided or woven mesh reinforcement material, such as polyethylene terephthalate (PET), nylon, metal or metallic fibers, or other suitable reinforcement material. The braided or woven mesh reinforcement layers are preferably porous, thereby providing the ability for a bonding material (described below) to penetrate the reinforcement layers.

In the embodiment, the body member 324 comprises a coil formed from a flat metal band that is wound into a spiral form. The coil may be formed from stainless steel, copper alloys, or other suitable metals or metallic materials. In other embodiments, the coil is formed of a rigid polymeric material. The coil structure of the body member 324 provides the shaft 302 with column strength and flexibility.

In the embodiment shown in FIGS. 16 and 17A-B, a bonding material extends through and bonds together each of the outer layer 322, body member 324, and inner layer 326. In the embodiment, the bonding material comprises a polymeric material such as plastisol that is applied using a dipping and/or spinning process. In one process for forming the shaft 302, the bonding material is applied to the outer layer 322, body member 324, and inner layer 326 while in a liquid form as the layers are retained on a mandrel, so that the bonding material is able to penetrate through each of the layers. After drying or curing the bonding material, the shaft 302 is removed from the mandrel. The outer layer 322, body member 324, and inner layer 326 are thereby bonded together. The reinforcement materials included in the outer layer 322 and inner layer 326 provide the composite shaft 302 with improved torque transmission capabilities relative to a shaft having, for example, only a single braided or woven layer on either the exterior or interior of a coil body member.

FIGS. 17A-B also show the tubes 344-350, steering wires 380, and steering wire coils 382 that extend through the shaft 302. In the embodiment shown, the tubes include two large diameter tubes 344, 346 having an ID of about 3 mm to about 9 mm, preferably about 6.3 mm, and two small diameter tubes 348, 350 having an ID of about 1.5 mm to about 7 mm, preferably about 4 mm. The outer diameter of the shaft 302 is preferably in the range of about 10 mm to about 30 mm. The steering wires 380 extend from the steering controls on the proximal handle 306 through the shaft 302 to the steering section 342 at the distal end of the shaft 302. The steering wire coils 382 receive and retain the steering wires 380. In the embodiment shown, the steering wire coils 382 are not formed integrally with or embedded in the composite shaft 302. Instead, the steering wire coils 382, along with the tubes 344-350, float within the inner lumen defined by the shaft 302.

Figure 18:
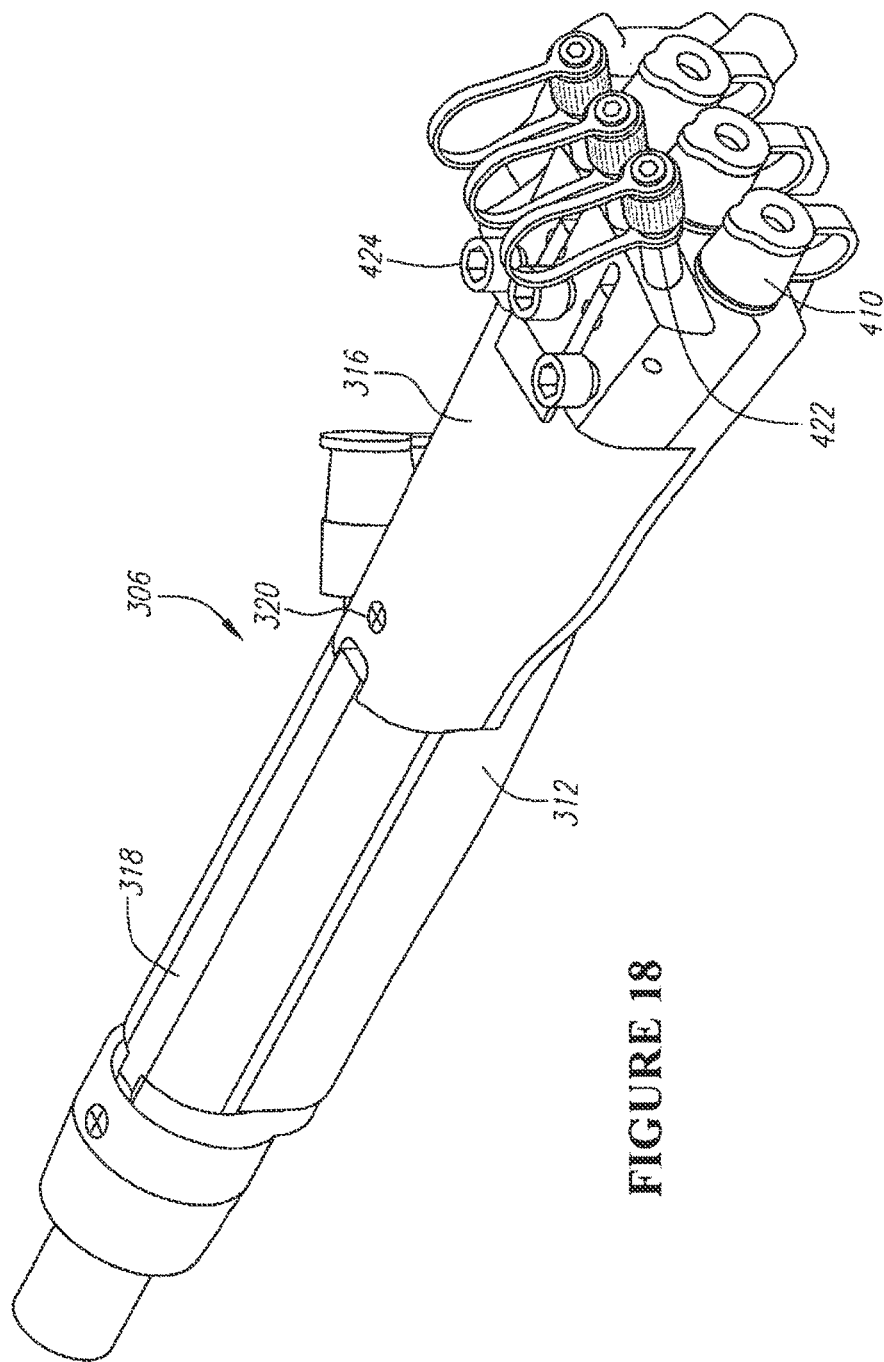
FIG. 18 is a perspective view of a handle of the endoscopic system of FIG. 16.
Figure 19:
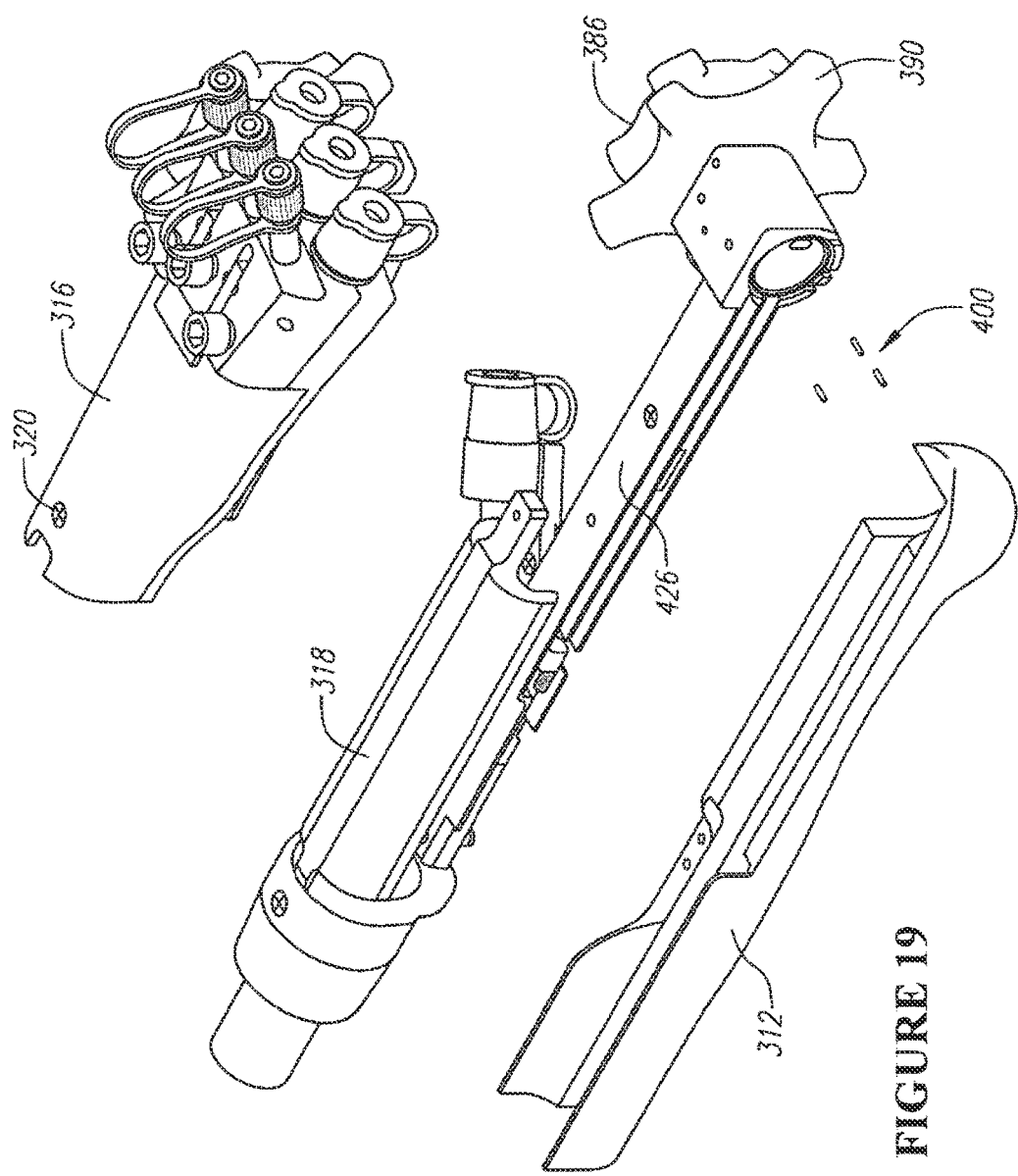
FIG. 19 is an exploded view of the handle of FIG. 18.
Figure 20:
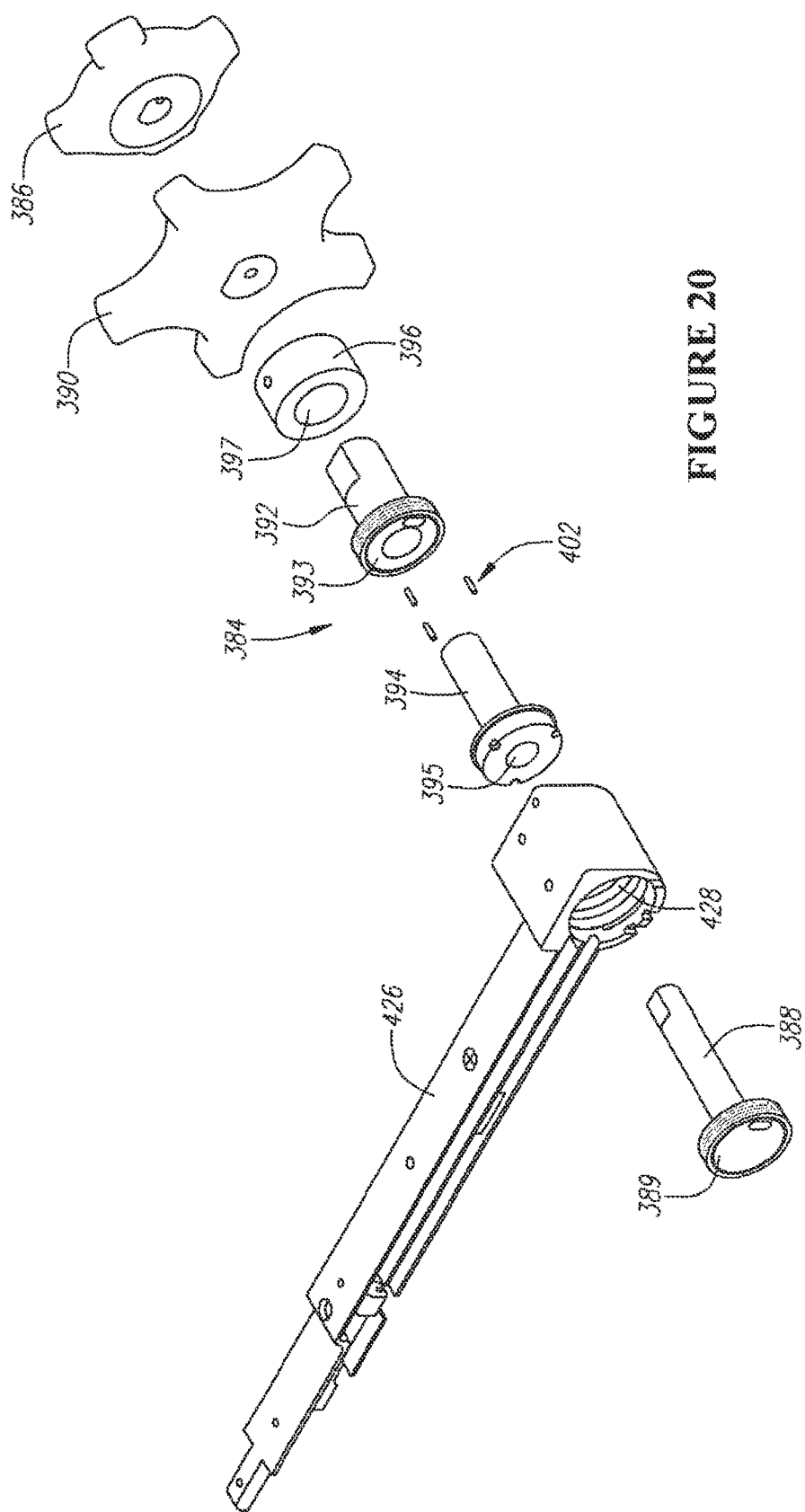
FIG. 20 is an exploded view of a steering assembly of the handle of FIGS. 18 and 19.

Turning to FIGS. 18 through 20, a handle 306 having an alternative steering assembly 384 is shown. The handle includes a tool manifold 430 having three lumen entry guides 410-414 and three luer ports 422, each of which provide access to one of the lumens defined by the tubes 344-350. Three screw-type tool locks 424 extend into three of the lumens to provide the ability to lock into place a tool that extends into the respective lumen. A center beam 426 is retained within the housing 310 and includes a bore 428 within which a portion of the steering assembly is housed.

The steering assembly 384 provides an alternative to the friction locking mechanisms used in conventional endoscopic devices. The assembly includes a small steering knob 386 that is attached to a first pulley 388, and a large steering knob 390 that is attached to a second pulley 392. In the embodiment, the steering knobs are attached to the shafts of their respective pulleys using a set screw (not shown). A main pulley shaft 394 having a center bore 395 is attached to the center beam 426 using a set screw (not shown). The shaft portion of the first pulley 388 extends through the center bore 395 of the main pulley shaft 394 and is thereby rotatably supported by the main pulley shaft 394, and the second pulley 392 rides on the external surface of the main pulley shaft 394 and is thereby also rotatably supported by the main pulley shaft 394. A bushing 396 having a center bore 397 is placed over the shaft of the second pulley 392 and is secured to the center beam 426 using a set screw (not shown).

Each of the first pulley 388 and second pulley 392 is, in turn, connected to a pair of steering wires 380 that extend to the steering section 342 of the device. Accordingly, rotating the small steering knob 386 and large steering knob 390 causes the first pulley 388 and second pulley 392, respectively, to selectively create tension in the steering wires 380 and to thereby steer the steering section 342 of the device. With four steering wires, the steering section 342 is capable of four-way steering. In other embodiments, more or fewer steering wires 380 are used to obtain desired steering performance.

As shown in FIG. 19, a set of three first pulley lock pins 400 are mounted to the inner surface of the lower housing 312 such that the pins 400 are aligned with the circumferential edge of the first pulley 388 and are substantially equidistant from one another. The facing surface of the first pulley 388 is provided with a plurality of circumferential holes 389 that are adapted to mate with the pins 400 as the first pulley 388 is shifted through the center bore 428 of the beam 426 toward the pins 400. In the embodiment shown, approximately 30 circumferentiales holes 389 are provided on the first pulley 388. In this way, the first pulley 388 is able to be locked in place relative to the housing 310 to provide indexed steering and positive locking.

Turning to FIG. 20, a set of three second pulley lock pins 402 are mounted to the surface of the main pulley shaft 394 facing the second pulley 392, such that the pins 402 are aligned with the circumferential edge of the second pulley 392 and are substantially equidistant from one another. The facing surface of the second pulley 392 is provided with a plurality of circumferential holes 393 that are adapted to mate with the pins 402 as the second pulley 392 is shifted through the center bore 428 of the beam 426 toward the pins 402. In the embodiment shown, approximately 30 circumferential holes 393 are provided on the second pulley 392. In this way, the second pulley 392 is able to be locked in place relative to the main pulley shaft 394 (which is fixed to the center beam 426) to provide indexed steering and positive locking.

Figure 21:
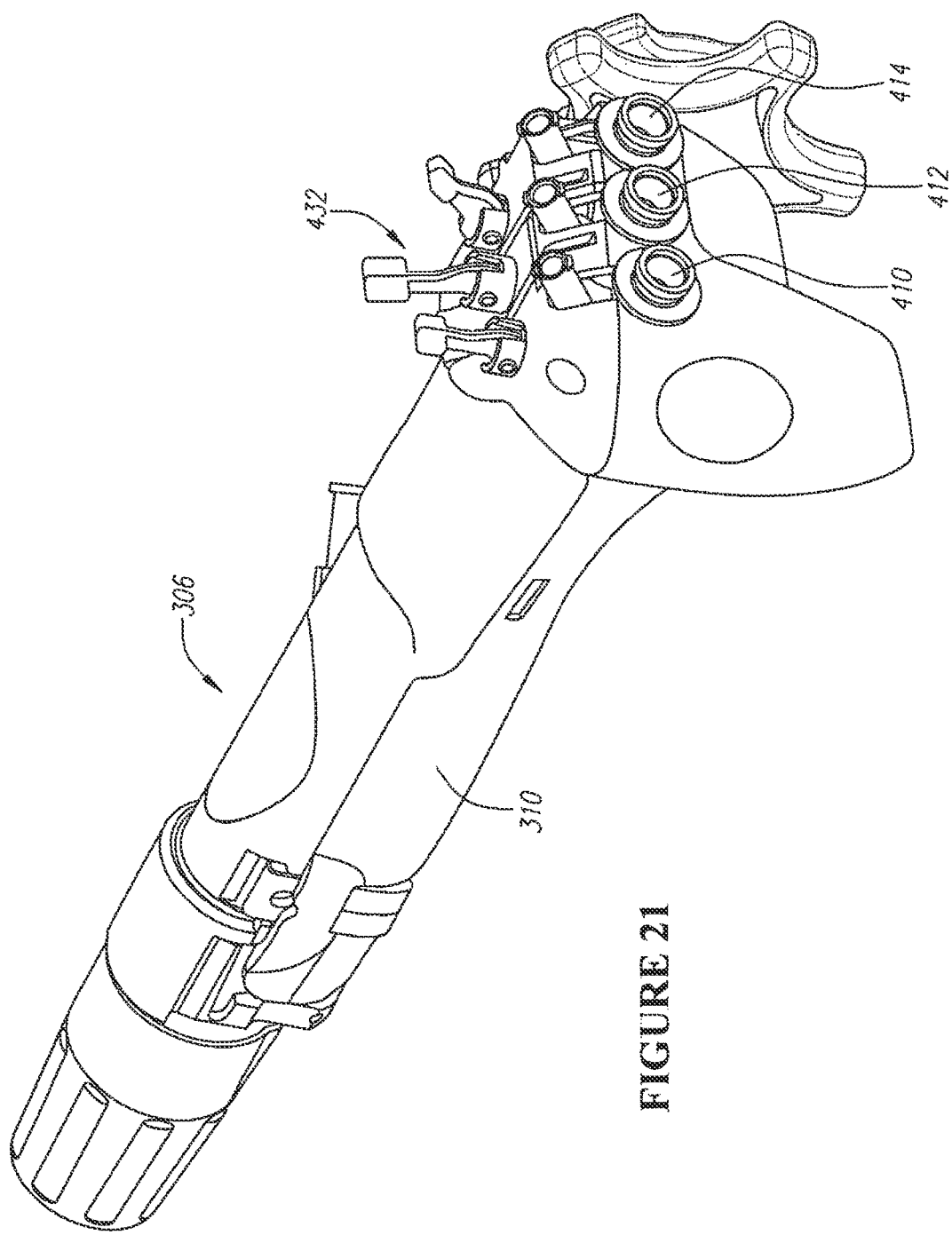
FIG. 21 is a perspective view of a handle of an alternative endoscopic system embodiment.
Figure 22:
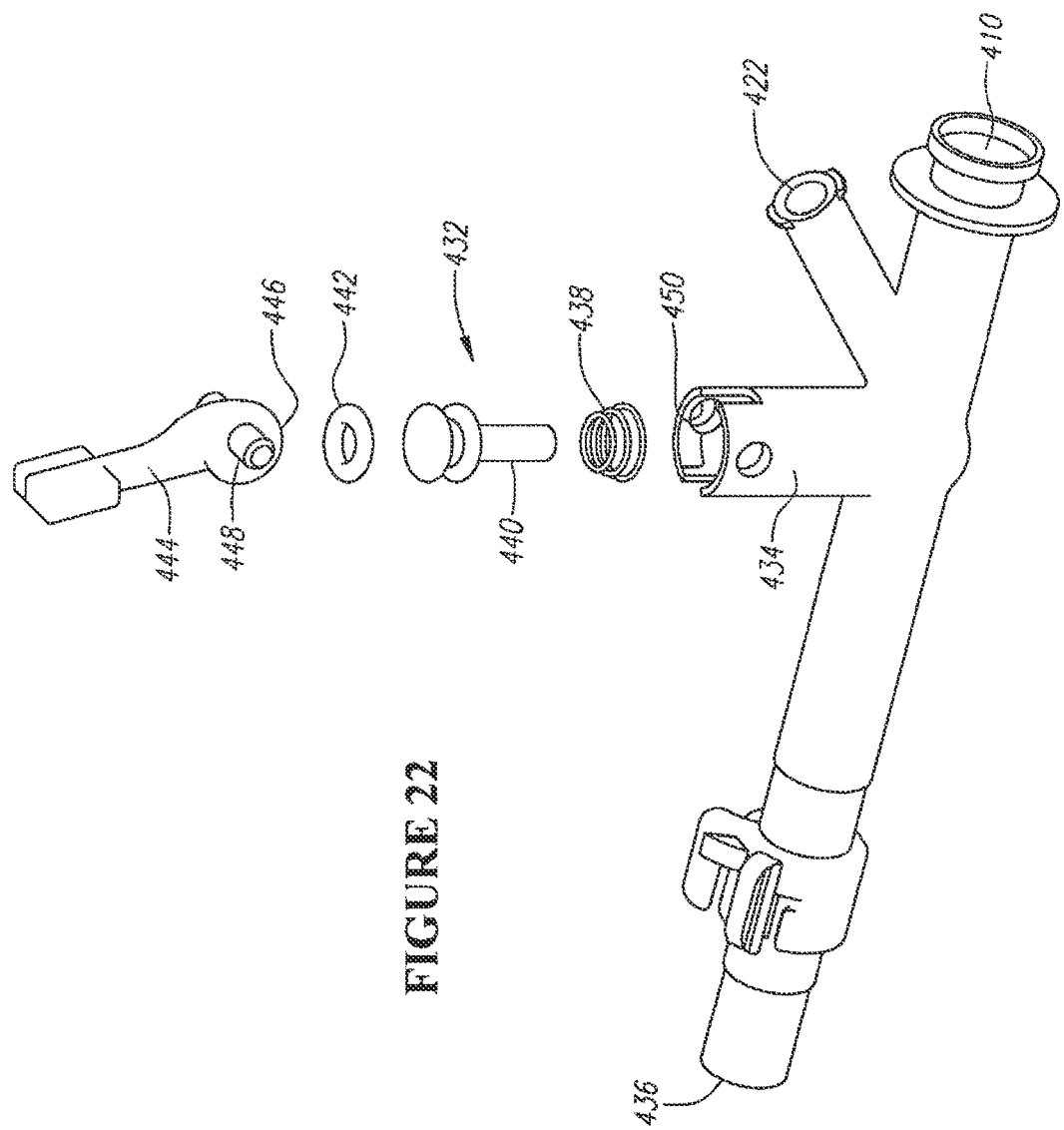
FIG. 22 is an exploded view of a toot locking mechanism of the handle of FIG. 21.

Turning next to FIGS. 21 and 22, an alternative tool locking mechanism 432 is shown. The tool locking mechanism 432 is an alternative to the screw-type mechanisms 124/424 such as those described above in relation to FIGS. 2 and 18. The tool locking mechanism 432 includes a cylindrical access port column 434 that extends substantially perpendicularly from a lumen 436 extending through the tool manifold 430. The access port column 434 defines a seat (not shown) within the column that is adapted to receive and retain a spring 438. A plunger 440 includes a shaft portion that extends through the spring 438, and a flange that rides upon the upper portion of the spring 438. In this way, the spring 438 provides a force biasing the plunger 440 upward within the access port column 434, away from the lumen 436. A seal 442, such as an O-ring, is retained between a pair of flanges on the plunger 440. The seal 442 prevents leakage of gas or liquids out of the access port column 434.

A lever 444 is mounted on the upper end of the access port column 434 such that a cam surface 446 of the lever 444 engages the upper surface of the plunger 440. In the embodiment shown, the lever 444 includes a pair of cylindrical tabs 448 that are retained in a mating pair of through holes 450 formed on the upper end of the access port column 434. Accordingly, the lever 444 is able to rotate about an axis defined by the cylindrical tabs 448. As the lever 444 rotates, the cam surface 446 causes the plunger 440 to be forced downward into the access port column 434 against the force of the spring 438. The plunger 440 shaft thereby engages a tool shaft that is located within the lumen 436, locking the tool shaft in place.

Figure 23:
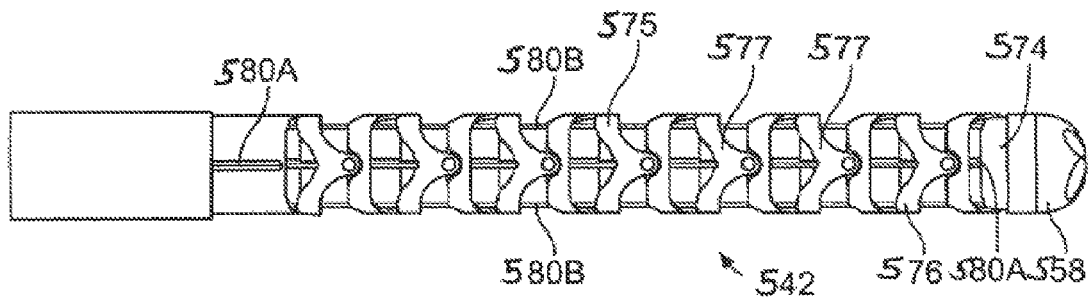
FIG. 23 is a side view of the distal end of a modification of the system of FIG. 1 with the sheath removed for purpose of illustration.
Figure 24:
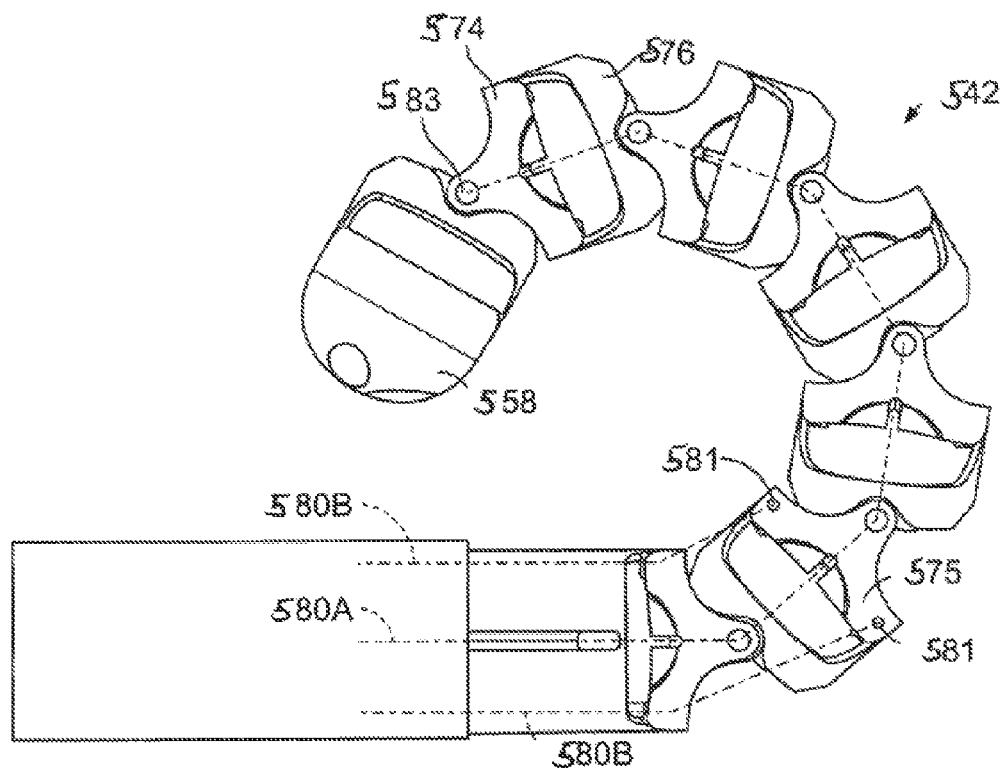
FIG. 24 is a side view of the system of FIG. 23 steered into a near maximum up position.

As shown in FIGS. 23 and 24, a first pair of steering wires 580A or other steering elements are attached onto opposite sides of the first link 574 at attachment points 583. Generally the first link 574 is the front or leading link which the tip 558 attached to. A second pair of steering wires 580B are attached to opposite sides of a second or proximal link 575 at attachment points 581. The proximal link 575 is spaced 4-30, 8-24 or 12-20 cm behind the first link 574, with several intervening links 577 between the first link 574 and the proximal link, for steering the steerable section 542. The steering wires 580A and 580B extend back from the first link 574 and the proximal link 575 and subsequent proximal links of the steering section 542, through the sheath 538 to the handle 536.

Alternatively, the subsequent proximal links, i.e., links between the handle and the proximal link 575 may be omitted and replaced with a tubular structure not having any links. The links are pivotally attached to each, with alternating angular positions, i.e., with even links pivotable in the up/down direction and with odd links pivotable in the left/right direction. The links are designed to allow at least 30, 35, 40, 45, or more degrees of pivot movement or angular rotation between adjoining links. The attachment of the second steering wires 580B onto the proximal link spaced behind the first link 574, and the pivoting capability of the links, allows the steerable end to be steered into a small bend radius. This makes the instrument highly maneuverable for use in endoluminal surgery.

Thus, novel methods and apparatus have been shown and described. Various changes and substitutions may of course be made without departing form the spirit and scope of the invention. The invention, therefore, should not be limited except by the following claims, and their equivalents.

The invention claimed is:

1. An endoscopic system, comprising,
   a flexible sheath body having a proximal non-steerable section adjoining a distal steerable section, with the distal steerable section including a distal link and a proximal link spaced proximally apart from the distal link by a plurality of intermediate links, and with each intermediate link pivotally attached to at least one adjacent intermediate link, the proximal link pivotally attached to a proximal intermediate link, with the proximal link at a distal end of the proximal non-steerable section, and with the proximal non-steerable section having no links, and the distal link pivotally attached to a distal intermediate link;
   a handle attached to the flexible sheath body;
   a first pulley rotatably supported on the handle;
   a plurality of first pulley lock projections adapted to rigidly engage into and withdraw from a corresponding plurality of first recesses in the first pulley, with the first pulley rotatable on the handle when the plurality of first pulley lock projections are disengaged from the plurality of first recesses, and with the first pulley rigidly locked against rotation on the handle when the plurality of first pulley lock projections are engaged into the plurality of first recesses;

a first steering wire wrapped around the first pulley and extending past the proximal link and attached to the distal link;

a second pulley rotatably supported on the handle;

a plurality of second pulley lock projections adapted to rigidly engage into and withdraw from a corresponding plurality of second recesses in the second pulley, with the second pulley rotatable on the handle when the plurality of second pulley lock projections are disengaged from the plurality of second recesses, and with the second pulley rigidly locked against rotation on the handle when the plurality of second pulley lock projections are engaged with the second plurality of recesses;

a second steering wire wrapped around the second pulley and terminating at the proximal link; and two or more lumens extending through the flexible sheath body.

2. The system of claim 1 with the second steering wire attached only to the proximal link.

3. The system of claim 1 with the first steering wire passing through openings in the proximal link.

4. An endoscopic system, comprising, a flexible sheath body having a proximal non-steerable section adjoining a distal steerable section, with the distal steerable section including a distal link and a proximal link spaced proximally apart from the distal link by a plurality of intermediate links, and with each intermediate link pivotally attached to at least one adjacent intermediate link, the proximal link pivotally attached to a proximal intermediate link, and the distal link pivotally attached to a distal intermediate link;

a handle attached to the flexible sheath body;

a main pulley shaft rigidly attached to the handle;

a first pulley having a first shaft extending through a center bore of the main pulley shaft, with the first pulley rotatably supported on the main pulley shaft;

a plurality of first pulley lock projections on the handle adapted to rigidly engage into and withdraw from a corresponding plurality of first recesses in the first pulley;

with the first pulley rotatable on the handle when the plurality of first pulley lock projections are disengaged from the plurality of first recesses, and with the first pulley rigidly locked against rotation on the handle when the plurality of first a first steering wire wrapped around the first pulley, extending through the proximal link and attached to the distal link;

a second pulley having a second shaft, with the main pulley shaft extending into the second shaft, and with the second pulley rotatably supported around the main pulley shaft;

a plurality of second pulley lock projections on the main pulley shaft adapted to rigidly engage into and withdraw from a corresponding plurality of second recesses in the second pulley;

with the second pulley rotatable on the handle when the plurality of second pulley lock projections are disengaged from the plurality of second recesses, and with the second pulley rigidly locked against rotation on the handle when the plurality of second pulley lock projections are engaged with the second plurality of recesses;

a second steering wire wrapped around the second pulley and attached only to and terminating at the proximal link; and two or more lumens in the flexible sheath body.

5. The system of claim 4 further including a center beam within the handle having a rear bore, and with the first shaft extending through the rear bore.

6. The system of claim 5 with the main pulley shaft attached to and extending out of the rear bore.

7. The system of claim 6 with the handle having a housing including a lower portion and an upper portion, with the manifold on the upper portion, and with the center beam between the lower portion and the upper portion.

8. An endoscopic system, comprising, a flexible sheath body having a proximal non-steerable section adjoining a distal steerable section, with the distal steerable section including a distal link and a proximal link spaced proximally apart from the distal link by a plurality of intermediate links, and with each intermediate link pivotally attached to at least one adjacent intermediate link, the proximal link pivotally attached to a proximal intermediate link, with the proximal link at a distal end of the proximal non-steerable section, and with the proximal non-steerable section having no links, and the distal link pivotally attached to a distal intermediate link;

a handle attached to the flexible sheath body;

a first pulley rotatably supported on the handle;

a plurality of first pulley lock projections adapted to rigidly engage into and withdraw from a corresponding plurality of first recesses in the first pulley, with the first pulley rotatable on the handle when the plurality of first pulley lock projections are disengaged from the plurality of first recesses, and with the first pulley rigidly locked against rotation on the handle when the plurality of first pulley lock projections are engaged into the plurality of first recesses;

a first steering wire wrapped around the first pulley and extending past the proximal link and attached to the distal link;

a second pulley rotatably supported on the handle;

a plurality of second pulley lock projections adapted to rigidly engage into and withdraw from a corresponding plurality of second recesses in the second pulley, with the second pulley rotatable on the handle when the plurality of second pulley lock projections are disengaged from the plurality of second recesses, and with the second pulley rigidly locked against rotation on the handle when the plurality of second pulley lock projections are engaged with the second plurality of recesses;

a second steering wire wrapped around the second pulley and terminating at the proximal link; and two or more lumens extending through the flexible sheath body.

* * * * *